United States Patent
Zurakowski

(10) Patent No.: US 9,874,563 B2
(45) Date of Patent: Jan. 23, 2018

(54) DETECTING AND QUANTIFYING CRYPTIC HIV REPLICATION

(71) Applicant: UNIVERSITY OF DELAWARE, Newark, DE (US)

(72) Inventor: Ryan Zurakowski, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 14/382,568

(22) PCT Filed: Mar. 7, 2013

(86) PCT No.: PCT/US2013/029503
§ 371 (c)(1),
(2) Date: Sep. 3, 2014

(87) PCT Pub. No.: WO2013/134458
PCT Pub. Date: Sep. 12, 2013

(65) Prior Publication Data
US 2015/0024381 A1    Jan. 22, 2015

Related U.S. Application Data

(60) Provisional application No. 61/607,772, filed on Mar. 7, 2012.

(51) Int. Cl.
*C12Q 1/70* (2006.01)
*G01N 33/569* (2006.01)

(52) U.S. Cl.
CPC ....... *G01N 33/56988* (2013.01); *C12Q 1/703* (2013.01); *C12Q 2600/136* (2013.01); *G01N 2800/52* (2013.01)

(58) Field of Classification Search
None
See application file for complete search history.

(56) References Cited

U.S. PATENT DOCUMENTS

| 7,232,657 | B2 | 6/2007 | Stevenson |
| 2002/0090611 | A1 | 7/2002 | Stevenson |
| 2003/0064054 | A1 | 4/2003 | Dong |
| 2008/0118494 | A1 | 5/2008 | Kutsch |
| 2008/0206742 | A1 | 8/2008 | Kalpana |
| 2011/0086048 | A1 | 4/2011 | Stevenson |
| 2012/0034597 | A1 | 2/2012 | Stevenson |

FOREIGN PATENT DOCUMENTS

WO    WO 2010/088491    *    4/2010

OTHER PUBLICATIONS

Josefsson et al., Curr Opin Infect Dis. 23(6):628-632 (2010).
Teo et al., J Immunol Methods 270: 109-118 (2002).
Panther et al., J Med Virol 58: 165-173 (1999).
Labbé, Journal of Pharmacokinetics and Pharmacodynamics 33(4): 519-542 (2006).
Wu and Wu, Stat Med 21: 753-771 (2002).
DEttorre et al., AIDS Res Hum Retroviruses 27(4): 1-10 (2011).
Geeraeft et al., Annu Rev Med 59: 487-501 (2008).
Chun et al., Nat Med 5(6): 651-655 (1999).
Van Praag et al., J Clin Immunol 21(3): 218-226 (2001).
Zhang, Int J Biochem Cell Biol 41: 451-454 (2009).
Ramratnam et al., Nat Med 6(1): 82-85 (2000).
Anderson et al., J Virol. 85(10):5220-5223 (2011).
Armbruster and Pry, Clin Biochem Rev. Aug. 2008;29 Suppl 1:S49-52.
Bailey et al., J Virol. 80(13):6441-6457 (2006).
Baldazzi et al., BMC Bioinformatics. 2009;10:387: 1-11.
Beltman et al., J Exp Med. Apr. 2007;204(4):771-780.
Bengtsson et al., BMC Mol Biol. 2008;9:63: 1-11.
Besson et al., Clinical Infectious Diseases. Jan. 2012;54(3):451-453.
Blazkova et al., 2009 PLoS Pathog 5(8): e1000554.
Bortz and Nelson, Bulletin of Mathematical Biology. 2006;68:2005-2025.
Bushman, AIDS. Mar. 2003;17(5):749-750.
Butler et al., J Virol. Apr. 2002;76(8):3739-3747.
Buzón et al., PLoS Pathog. Oct. 2011;7(10):e1002314.
Buzón et al., Nat Med. Apr. 2010;16(4):460-465.
Callaway et al., Bull Math Biol. Jan. 2002;64(1):29-64.
Cardozo et al., In: 51st IEEE Conference on Decision and Control. Maui, HI; 2012. p. 4924-4929.
Chen et al., 2007 Proc Natl Acad USA 104(48): 19079-19084.
Chun et al., Nat Med 6(7):757-761 (2000).
Chun et al., Nature 401(6756):874-875 (1999).
Cintron-Arias et al., Math Biosci Eng. 6(2):261-282 (2009).
Cohen, Science 334(6063):1614 (2011).
Colgrove and Japour, Antiviral Res. Feb. 1999;41(1):45-56.
Crosley et al., Genes Nutr. Jun. 2009;4(2):95-102.
Davey et al., Proc Natl Acad Aci U S A. 96(26):15109-15114 (1999).
De Boer et al., 2010 PLoS Comput Biol 6(9): e1000906.
Dinoso et al., Proc Natl Acad U.S.A. 106(23):9403-9408 (2009).
DiStefano and Cobelli, IEEE Transactions on Automatic Control. 1980;25(4):830-833.
Dornadula et al., JAMA. 282(17):1627-1632 (1999).
Evering et al., PLoS Pathog. 8(2):e1002506 (2012).
Fraser et al., 2000 AIDS 14(6): 659-669.
Friedrich et al., Virol J. 2010;7:354: 1-6.

(Continued)

*Primary Examiner* — Nicole Kinsey White
(74) *Attorney, Agent, or Firm* — RatnerPrestia

(57) ABSTRACT

The present invention relates to a novel method for detecting efficient cryptic HIV replication in a patient who receives a suppressive antiviral therapy followed by administration of the HIV integrase inhibitor in an effective amount for intensifying the suppressive antiviral therapy, and has undetectable plasma viremia prior to the administration of the HIV integrase inhibitor. The method comprises making a pre-intensification measurement and one or more post-intensification measurements of the concentration of an episomal artifact in samples from the patient, and computing a pre-intensification HIV infection success ratio (R). A pre-intensification HIV infection success ratio (R) sufficiently close to 1 indicates that the patient has the efficient cryptic HIV replication. The method may further comprise quantifying the efficient cryptic HIV replication.

9 Claims, 10 Drawing Sheets

(56) References Cited

OTHER PUBLICATIONS

Gandhi et al., J Acquir Immune Defic Syndr. 59(3):229-235 (2012).
Girard et al., Nat Rev Immunol. Nov. 2012;12(11):762-773.
Han et al., In: Gatsonis et al., editors, Case Studies in Bayesian Statistics. New York: Springer; 2002. p. 223-237.
Halano et al., AIDS 14(10):1357-1363 (2000).
Halano et al., AIDS 24(16):2535-2539 (2010).
Hermankova et al., JAMA. 286(2):196-207 (2001).
Hockett et al., 1999 J Exp Med 189(10): 1545-1554.
Huang et al., Biom J. Jul. 2010;52(4):470-486.
International Preliminary Report on Patentability for International Application No. PCT/US2013/029503 dated Sep. 9, 2014.
International Search Report for International Application No. PCT/US2013/029503 dated Jun. 20, 2013.
Kieffer et al., J Infect Dis. 189(8):1452-1465 (2004).
Kirschner et al., J Acquir Immune Defic Syndr. Aug. 2000;24(4):352-362.
Lafeuillade et al., 2001 HIB Medicine 2: 189-194.
Lai et al., Biophys J. Nov. 2009;97(9):2379-2387.
Lambotte et al., AIDS 18(8):1147-1158 (2004).
Llibre et al.. Antivir Ther (Lond). Jun. 2012;17:355-364.
Luo et al., J Clin Microbiol, Jul. 2012;50(10):3381-3382.
Luo et al., Journal of the Royal Society Interface; 2013; 10; 1-12.
Luo et al., PLoS One. Jul. 2012;7(7):e40198.
Maldarelli, Curr Op in HIV AIDS. 6(1);49-56 (2011).
Maldarelli et al., PLoS Pathog. 3(4):e46 (2007).
Marinho et al., Physica A. Jan. 2012;391(1-2):132-141.
Markowitz et al., J Virol. Apr. 2003;77(8):5037-5038.
McMahon et al., Clinical Infectious Diseases. 50(6):912-919 (2010).
Miao et al., Biometrics. 2009;65:292-300.
Miao et al., SIAM Rev Soc Ind Appl Math, Jan. 2011;53(1):3-39.
Mirsky et al., J Theor Biol. Oct. 2011;287:160-170.
Morlese et al., AIDS. Mar. 2003;17(5);679-683.
Murray, Antivir Chem Chemother. 2009;19(4):157-164.
Murray and Jackson, Mar Ecol Prog Ser. Nov. 1992;89:103-116.
Murray et al., AIDS. Nov. 2007;21(17):2315-2321.
Nettles et al., JAMA. 293(7):817-829 (2005).
Orenstein et al., AIDS. Nov. 1999;13(16):2219-2229.
Palmer et al., J Clin Microbiol. 41(10):4531-4536 (2003).
Pauza et al., Virology. 1994; 205(2):470-478.
Perelson, Mathematical Biosciences. 1993:114(1):81-125.
Perrin et al., J Clin Microbiol. Dec. 2006;44(12):4371-4375.
Persaud et al., J Viral, 78(2):968-979 (2004).
Pierson et al., J Virol. Apr. 2002;76(8):4138-4144.
Prins et al., 1999 AIDS 13(17): 2405-2410.
Pulter et al., Stat Med. Aug. 2002;21(15):2199-2214.
Reigadas et al., J Antimicrob Chemother. Mar. 2010;65(3):434-437.
Ribeiro and Bonhoeffer 2000 Proc Natl Acad Sci UDS 97(14): 7681-7686.
Rong and Perelson, PLoS Comput Biol. Oct. 2009;5(10):e1000533.
Rong and Perelson 2009 Math Biosci 217(1): 77-87.
Rong and Perelson 2009 J Thero Biol 260(2): 308-331.
Samson et al., Computational Statistics & Data Analysis. 2006; 51(3):1562-1574.
Sedaghat et al, Antivir Ther. 2009;14(2):263-271.
Sharkey at al., Nat Med. Jan. 2000;6(1):76-81.
Sharkey et al., PLoS Pathog. 7(2):e1001303 (2011).
Siliciano and Siliciano, Curr Opin HIV AIDS 5(6):491-497 (2010).
Siliciano and Siliciano 2004 J Antimicrob Chemother 54(1): 6-9.
Song et al., 2003 J Virol 77(13): 7174-7181.
Stellbrink et al,, 2002 AIDS 16(11): 1479-1487.
Swartz, Adv Drug Deliv Rev. 2001; 50(1-2):3-20.
Tobin, Econometrica. Jan. 1958;26(1):24-36.
Tobin et al., J Virol. 79(15):9625-9634 (2005).
Trono et al., Science 329(5988):174-180 (2010).
Tse and Anton, IEEE Transactions on Automatic Control. 1972;17(5):637-646.
von Andrian and Mempel, Nat Rev Immunol. Nov. 2003;3(11):867-878.
Wong et al., J Virol. Mar. 1997;71(3):2059-2071.
Wong et al., Science 278(5341):1291-1295 (1997).
Wu, Statistical Methods in Medical Research. 2005;14:171-192.
Wu and Wu, Journal of the Royal Statistical Society Series C (Applied Statistics). Jan. 2002;51(3):297-318.
Wu et al., 2005 J Acquir Immune Defic Syndr 39(3): 272-283.
Wu et al., Biom J. Apr. 2004;46(2):233-245.
Wu et al., Bull Math Biol. Apr. 2008;70(3):785-799.
Yuki et al., AIDS. Oct. 2010;24(16):2451-2460.
Zhu et al., J Virol. May 1996;70(5):3098-3107.
Zhu et al., PLoS ONE. 2011;6(6):e21081.

\* cited by examiner

DETECTING AND QUANTIFYING CRYPTIC HIV REPLICATION

CROSS-REFERENCE TO RELATED APPLICATION

This application is a U.S. National Phase Application of PCT International Application No. PCT/US2013/029503, filed Mar. 7, 2013, which claims the benefit of U.S. Provisional Application No. 61/607,772, filed Mar. 7, 2012, the contents of each of which are incorporated herein by reference in their entireties for all purposes.

REFERENCE TO U.S. GOVERNMENT SUPPORT

This invention was made with government support under Grant Numbers R21AI078842, RO1 AI087135 and P30 AI078498 awarded by the National Institute of Allergy and Infectious Diseases. The United States has certain rights in the invention.

FIELD OF THE INVENTION

The invention relates generally to detection and quantification of cryptic human immunodeficiency virus (HIV) replication in patients receiving a suppressive antiviral therapy.

BACKGROUND OF THE INVENTION

While numerous antiviral drugs have been developed and approved for treating HIV patients, none of them eliminates HIV completely from the patients. Rather, these antiviral drugs suppress HIV replication in the patients, and are often used in combination to achieve best therapeutic effects in patients. Highly-Active Antiretroviral Therapy (HAART) is a combination therapy capable of suppressing HIV viral replication below the limit of detection in many patients. The rapid rebound of viremia following treatment interruption indicates that HAART is unable to eradicate the virus. Low levels of viremia have also been detected in many patients using ultrasensitive viral load assays with sensitivity down to 1 virion per ml plasma. It is accepted that low-level viremia persists during effective suppression by HAART; it is unclear whether this viremia derives primarily from the activation of stable viral reservoirs such as the latently infected memory-phenotype CD4+ T cells, or ongoing rounds of successful infection of active CD4+ T cells, or a combination of the two. Furthermore, some evidence exists for continued replication of the virus in cryptic reservoirs despite suppression below the standard limit of detection. This may be due to tissue-dependent distribution and efficacy of the antiviral agents.

Understanding the origin of cryptic and residual viremia under suppressed conditions is important for a number of reasons. HIV mutations arise primarily during the process of reverse transcription during the de novo infection of active CD4+ T cells. If the viremia is driven primarily by the de novo infection of active CD4+ T cells, it represents an ongoing source of viral mutants that could eventually result in mutational escape from antiviral therapy. The activation of reservoir cells, which does not involve a new round of reverse transcription, does not result in the production of new viral mutants, and cannot by itself drive the evolution of antiviral resistance.

Genotypic studies of the residual plasma viremia have shown little or no development of new resistance mutations, which has been interpreted as evidence that residual viremia is primarily the result of activation of quiescent reservoirs. Recent analysis of HIV envelope proteins in the gut-associated lymphoid tissue (GALT) has likewise shown no evidence of evolution during suppressive therapy. Treatment intensification has consistently shown no significant decrease in the residual plasma viremia. Conversely, a genotypic study focused on episomal cDNA collected prior to viral rebound indicated that the episomal cDNA showed evidence of recent evolution, implying de novo replication as the source.

Many authors have suggested using episomal artifacts of HIV infection as surrogate markers of replication, including linear unintegrated DNA, 1-LTR, and 2-LTR circular DNA. 2-LTR artifacts are especially useful as the 2-LTR region of the genome is unique to the episomal artifact as compared to linear integrated DNA. However, the use of 2-LTR as a surrogate marker is controversial, primarily due to controversy regarding the half-life of the episomes. 2-LTR circles have been shown to be stable in vitro, leading to the conclusion that they are not an effective surrogate measurement of recent infection. Studies estimating the half-life of the circles in vivo, however, indicate that they are highly labile, with half-lives of only a few days. One possible explanation is that the host cells may have significantly shorter half-lives in vivo than in vitro, possibly due to a high likelihood of programmed proliferation in 2-LTR-containing cells.

There remains a need for reliable methods to detect cryptic viremia in patients receiving a suppressive antiviral therapy for assessing or predicting the efficacy of the suppressive antiviral therapy.

SUMMARY OF THE INVENTION

The present invention relates to methods for detecting efficient cryptic HIV replication in a patient and related systems.

According to one aspect of the present invention, a method for detecting efficient cryptic HIV replication in a patient is provided. The patient receives a suppressive antiviral therapy not containing an HIV integrase inhibitor followed by administration of the HIV integrase inhibitor in an effective amount for intensifying the suppressive antiviral therapy, and the patient has undetectable plasma viremia prior to the administration of the HIV integrase inhibitor. The method comprises: (a) making a pre-intensification measurement of the concentration of an episomal artifact in a pre-intensification sample from the patient; (b) making one or more post-intensification measurements of the concentration of the episomal artifact in one or more post-intensification samples from the patient; and (c) computing, on at least one processor, a pre-intensification HIV infection success ratio (R) based on the pre-intensification measurement and the one or more post-intensification measurements. A pre-intensification HIV infection success ratio (R) sufficiently close to 1 indicates that the patient has the efficient cryptic HIV replication. The method may further comprise administering the HIV integrase inhibitor to the patient.

Where the patient has efficient cryptic HIV replication, the method may further comprises quantifying the efficient cryptic HIV replication. The quantifying step may comprise computing, on at least one processor, the magnitude of a pre-intensification HIV infected-cell turnover rate (ay(0)) based on the pre-intensification measurement and the one or more post-intensification measurements. The method may further comprise improving the suppressive antiviral therapy for the patient based on the magnitude of the pre-intensification HIV infected-cell turnover rate (ay(0)). After the improvement, the pre-intensification HIV infection success ratio (R) may be reduced to less than about 0.99, 0.95, 0.9, 0.8, 0.7, 0.6, 0.5, 0.4, 0.3, 0.2, 0.1, 0.05, preferably less than about 0.8.

In the method according to the present invention, the patient may have received the suppressive antiviral therapy for at least about 1 week, 2 weeks, 4 weeks, 1 month, 2 months, 3 months, 6 months, 12 months or 24 months, preferably for at least about 6 months, prior to the administration of the HIV integrase inhibitor. The HIV integrase inhibitor may be raltegravir or elvategravir, preferably raltegravir. The episomal artifact may be selected from the group consisting of linear unintegrated HIV DNA, HIV 1-LTR DNA, and HIV 2-LTR circular DNA. Each of the pre-intensification sample and the one or more post-intensification samples may be a whole blood sample.

The intensification may last for at least about 2, 4, 6, 8, 12, 18, 24, 36 or 48 weeks, preferably for at least about 4 weeks. The one or more post-intensification measurements may be made daily, weekly, bi-weekly, monthly or bi-monthly, preferably weekly. The one or more post-intensification measurements may be 1, 2, 3, 4, 5, 6, 7, 8, 9, 10, or more, preferably 4, post-intensification measurements, and may comprise a post-intensification measurement of a peak concentration of the episomal artifact ($C_p$).

In one embodiment, the method may further comprise computing, on at least one processor, the pre-intensification HIV infection success ratio (R) based on one or more values selected from the group consisting of a death rate of actively infected cells (a), a rate of production of actively infected cells by processes other than infection ($y_e$), ratio-reduction in R following the intensification ($\eta_{II}$), a ratio of the probability of the episomal artifact formation during an infection event when the HIV integrase inhibitor is not present to the probability of the episomal artifact formation when the HIV integrase inhibitor interrupts an infection event ($\varphi$), probability of the episomal artifact formation when the HIV integrase inhibitor interrupts an infection event ($k_{II}$), a decay rate of the episomal artifact ($\delta$), a post-intensification peak concentration of the episomal artifact ($C_p$), a concentration of peripheral blood mononuclear cells (PBMCs) in a whole blood sample ($PMBC_m$), an effective volume of the patient ($V_e$), one or more measurements of plasma viral load v(t), and the associated measurement times (t).

In another embodiment, the method may further comprise computing, on at least one processor, the pre-intensification HIV infection success ratio (R) based on one or more values selected from the group consisting of a death rate of actively infected cells (a), a rate of production of actively infected cells by processes other than infection ($y_e$), ratio-reduction in R following the intensification ($\eta_{II}$), a ratio of the probability of the episomal artifact formation during an infection event when the HIV integrase inhibitor is not present to the probability of the episomal artifact formation when the HIV integrase inhibitor interrupts an infection event ($\varphi$), probability of the episomal artifact formation when the HIV integrase inhibitor interrupts an infection event ($k_{II}$), and a decay rate of the episomal artifact ($\delta$).

According to anther aspect of the present invention, a system is provided for each method of the present invention. A system for detecting efficient cryptic HIV replication in a patient comprises at least one processor and a compute readable medium coupled to the at least one processor, having instructions which when executed cause the at least one processor to compute a pre-intensification HIV infection success ratio (R). The patient receives a suppressive antiviral therapy not containing an HIV integrase inhibitor followed by administration of the HIV integrase inhibitor in an effective amount for intensifying the suppressive antiviral therapy, and has undetectable plasma viremia prior to the administration of the HIV integrase inhibitor. The pre-intensification HIV infection success ratio (R) is computed based on (a) a pre-intensification measurement of the concentration of an episomal artifact in a pre-intensification sample from the patient, and (b) one or more post-intensification measurements of the concentration of the episomal artifact in one or more post-intensification samples from the patient.

In some embodiments, the instructions of the computer readable medium in the system may when executed further cause the at least one processor to compute the pre-intensification HIV infection success ratio (R) based on one or more values selected from the group consisting of a death rate of actively infected cells (a), a rate of production of actively infected cells by processes other than infection ($y_e$), ratio-reduction in R following the intensification ($\eta_{II}$), a ratio of the probability of the episomal artifact formation during an infection event when the HIV integrase inhibitor is not present to the probability of the episomal artifact formation when the HIV integrase inhibitor interrupts an infection event ($\varphi$), probability of the episomal artifact formation when the HIV integrase inhibitor interrupts an infection event ($k_{II}$), a decay rate of the episomal artifact ($\delta$), a post-intensification peak concentration of the episomal artifact ($C_p$), a concentration of peripheral blood mononuclear cells (PBMCs) in a whole blood sample ($PMBC_m$), an effective volume of the patient ($V_e$), one or more measurements of plasma viral load v(t), and the associated measurement times (t).

In other embodiments, the instructions of the computer readable medium in the system may when executed further cause the at least one processor to compute the pre-intensification HIV infection success ratio (R) based on one or more values selected from the group consisting of a death rate of actively infected cells (a), a rate of production of actively infected cells by processes other than infection ($y_e$), ratio-reduction in R following the intensification ($\eta_{II}$), a ratio of the probability of the episomal artifact formation during an infection event when the HIV integrase inhibitor is not present to the probability of the episomal artifact formation when the HIV integrase inhibitor interrupts an infection event ($\varphi$), probability of the episomal artifact formation when the HIV integrase inhibitor interrupts an infection event ($k_{II}$), and a decay rate of the episomal artifact ($\delta$).

In yet some other embodiments, the instructions of the computer readable medium in the system may when executed further cause the at least one processor to compute a pre-intensification HIV infected-cell turnover rate (ay(O)) based on the pre-intensification measurement and the one or more post-intensification measurements.

DETAILED DESCRIPTION OF THE INVENTION

Figure 1:
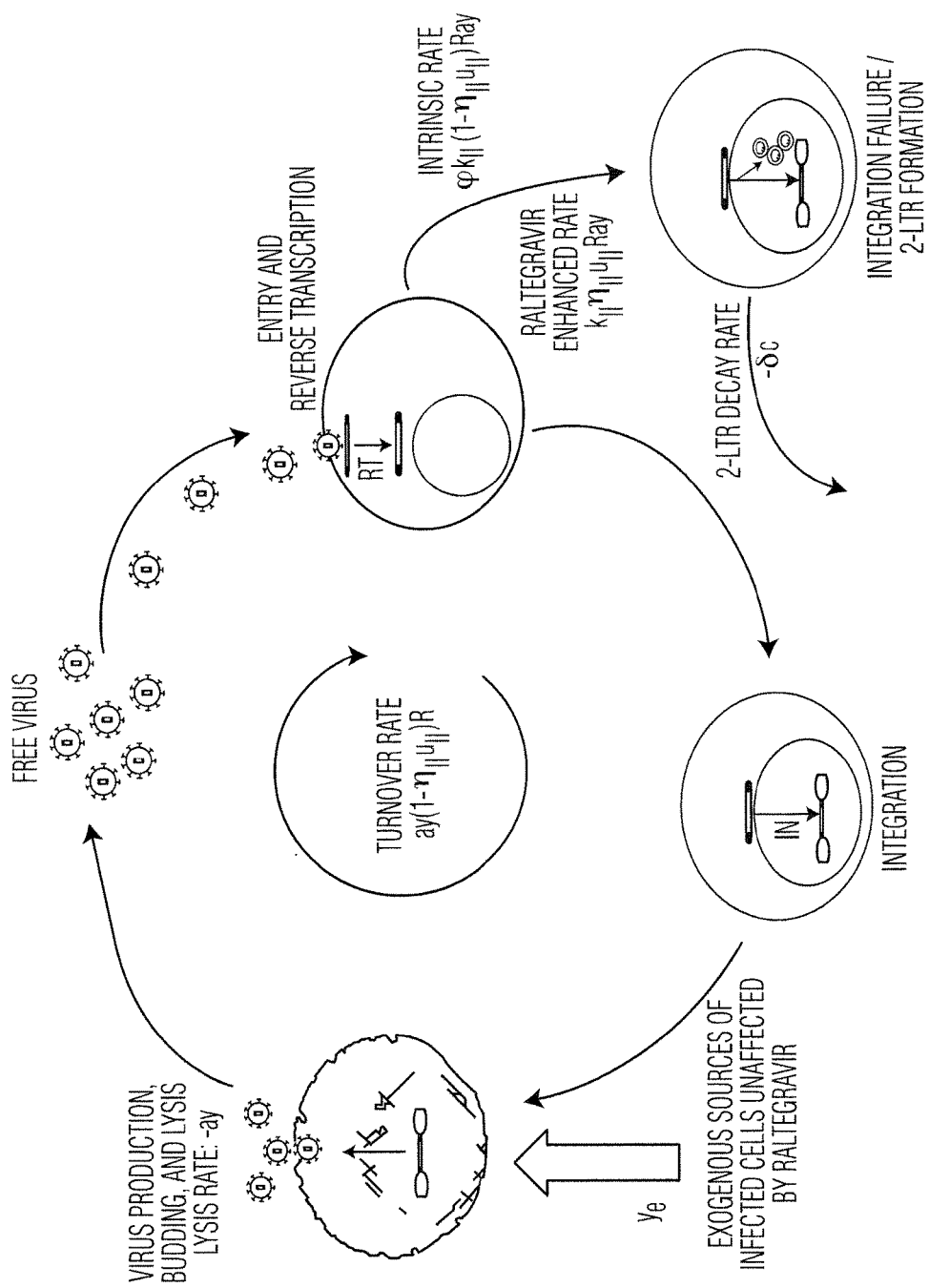
FIG. 1 illustrates virus life cycle. In the site of 2-LTR formation, free virus enters target cells, then undergoes reverse transcription and integration. The infected cell then produces virus and lyses, completing the cycle with a turnover rate of ayR before raltegravir intensification and ay(1−$\eta_{II}$)R after raltegravir intensification. Active infected cells may also come from exogenous sources not affected by raltegravir at a rate $y_e$; these sources include but are not limited to activation of quiescent reservoir cells and efficient replication in sites unaffected by raltegravir. Integration failure and 2-LTR formation occurs at an intrinsic rate which is proportional to the successful infection rate, $ay\varphi k_{II}R$ before raltegravir intensification or $ay\varphi k_{II}(1-\eta_{II})R$ after intensification. The rate of 2-LTR formation in cells affected by raltegravir is proportional to the inhibitory effect of raltegravir, $ak_{II}\eta_{II}R$. 2-LTR-containing cells decay at a rate $\delta$.

The present invention relates to a novel method for detecting and quantifying cryptic HIV replication in patients receiving a suppressive antiviral therapy. This method is useful for assessing or predicting the efficacy of the suppressive antiviral therapy in patients having undetectable plasma viremia.

Various assays have been developed to detect and quantify HIV in a subject based on detection of an HIV antibody, antigen or RNA in a sample from the subject, for example, serum, saliva or urine. A standard HIV detection assay may be any HIV detection assay used to detect and/or quantify the presence of HIV in a human patient, for example, an assay detecting HIV RNA in a sample by amplification of the HIV RNA or a fragment thereof using real-time PCR (qPCR) or droplet digital PCR, antibody tests including ELISA, western blot, and/or indirect immunofluorescence assays. A standard HIV detection assay may detect as low as about 500, 100, 50, 10 or 1 virion per ml in a sample.

The present invention provides a method for detecting efficient cryptic HIV replication in a patient. The patient receives a suppressive antiviral therapy not containing an HIV integrase inhibitor followed by the HIV integrase inhibitor in an effective amount for intensifying the suppressive antiviral therapy. The patient has undetectable plasma viremia (e.g., less than 50 virions per mL of whole blood) prior to the administration of the integrase inhibitor. The method comprises: (a) making a pre-intensification measurement of the concentration of an episomal artifact in a pre-intensification sample from the patient; (b) making one or more post-intensification measurements of the concentration of the episomal artifact in one or more post-intensification samples from the patient; and (c) computing, on at least one processor, a pre-intensification HIV infection success ratio (R) based on the pre-intensification measurement and the one or more post-intensification measurements. A pre-intensification HIV infection success ratio (R) sufficiently close to 1 indicates that the patient has the efficient cryptic HIV replication.

The term "efficient cryptic HIV replication" used herein refers to ongoing HIV replication undetectable by a standard HIV detection assay. HIV replication may be detected using any suitable HIV detection assay, preferably a standard HIV detection assay (e.g., real-time PCR (qPCR) or droplet digital PCR). Efficient cryptic HIV replication in a patient receiving a suppressive antiviral therapy is not controlled by the therapy.

The term "a suppressive antiviral therapy" as used herein refers to an antiviral regimen containing a single drug or multiple drugs in an effective amount for reducing HIV replication in a patient. The reduction may be by at least about 1 $\log_{10}$, preferably 2-5 $\log_{10}$ depending on pre-treatment viral load, and most preferably durably suppressed to a plasma viral load of less than 50 copies per ml. An example of the suppressive antiviral therapy is the Highly-Active Antiretroviral Therapy ("HAART"), which contains reverse transcriptase inhibitors and/or protease inhibitors, and significantly reduces HIV replication in the majority of HIV infected patients.

The term "undetectable plasma viremia" is used herein as referring to a medical condition of a patient, where HIV in the patient's bloodstream is below a detectable level when the patient receives a suppressive antiviral therapy, but becomes detectable when the suppressive antiviral therapy is interrupted. The term "cryptic viremia" is used herein as referring to a medical condition of a patient where undetectable plasma viremia co-exists with ongoing HIV replication occurring in a remote anatomical site. HIV detection may be carried out using any suitable HIV detection assay, preferably a standard HIV detection assay (e.g., real-time PCR (qPCR) or droplet digital PCR). A patient having undetectable plasma viremia may have less than about 100, 50, 10, 5 or 1 virion in a plasma sample from the patient as detected and quantified in a standard HIV detection assay (e.g., real-time PCR (qPCR) or droplet digital PCR).

The term "intensifying" as used herein means improving or enhancing. Intensification of a suppressive antiviral therapy improves or enhances the efficacy of the suppressive antiviral therapy. For example, the intensification may further reduce the HIV replicative success ratio by, for example, at least about 5%, 10%, 20%, 30%, 40%, 50%, 60%, 70%, 80%, 90%, 95% or 99%, preferably by at least 90%, in a patient, who has received the suppressive antiviral therapy for a period of time, for example, for at least about 1 week, 2 weeks, 4 weeks, 1 month, 2 months, 3 months, 6 months, 12 months or 24 months, preferably for at least about 6 months, before the intensification. The intensification period lasts for a period of time sufficient to observe the effects of intensification on an episomal artifact, for example, at least about 2, 4, 6, 8, 12, 18, 24, 36 or 48 weeks, preferably for at least about 4 weeks.

An HIV integrase inhibitor may be any integrase inhibitor that reduces the likelihood of integration of HIV DNA or a fragment thereof into the genome of a host cell following viral entry and reverse-transcription. The reduction may be by at least about 5%, 10%, 20%, 30%, 40%, 50%, 60%, 70%, 80%, 90%, 95% or 99%, preferably by at least 50%, more preferably by at least 90%. For example, the HIV integrase inhibitor may be raltegravir or elvatigravir, preferably raltegravir. The HIV integrase inhibitor may be administered to a patient in a pharmaceutical composition as a single drug antiviral therapy or combined with other antiviral drugs in a multi-drug therapy. Preferably, the HIV integrase is suitable for a single antiviral drug therapy (e.g., raltegravir) so that toxicities of other antiviral drugs in a multi-drug formulation are avoided. The method of the present invention may further comprise administering an HIV integrase inhibitor to the patient.

The term "an effective amount" as used herein refers to an amount of an HIV integrase inhibitor required to achieve a stated goal (e.g., intensifying the efficacy of a suppressive antiviral therapy). The effective amount of an HIV integrase inhibitor in a patient may vary depending upon the stated goal, the physical characteristics of the patient, the nature and severity of HIV infection, existence of related or unrelated medical conditions, the nature of the HIV integrase inhibitor, the pharmaceutical composition comprising the HIV integrase inhibitor, the means of administering the pharmaceutical composition to the patient, and the administration route. A specific dose for a given patient may generally be set by the judgment of a physician or by routine experimentation. The pharmaceutical composition may be administered to the patient in one or multiple doses.

The term "patient" as used herein refers to a subject infected by HIV. The patient receives a suppressive antiviral therapy, and then receives an HIV integrase inhibitor to intensify the suppressive antiviral therapy. Before the intensification, the patient has undetectable plasma viremia, and may have received the suppressive antiviral therapy for at least about 0.5, 1, 2, 3, 6, 9, 12, 18 or 24 months, preferably for at least 6 months. The patient may have less than about 50 copies of HIV virions per ml plasma prior to the intensification.

The term "an episomal artifact" as used herein refers to an HIV DNA transcript which is not integrated into the host cell's chromosomes. Examples of an episomal artifact include linear unintegrated HIV DNA, HIV 1-LTR circular DNA, and HIV 2-LTR circular DNA. Preferably, the episomal artifact is HIV 2-LTR circular DNA (hereinafter also referred to as "2-LTR"). The concentration of an episomal artifact may be measured or determined using techniques known in the art. For example, the concentration of the episomal artifact may be measured based on the amount of a unique nucleotide sequence in the episomal artifact.

The term "pre-intensification measurement" used herein refers to a measurement of the concentration of an episomal artifact in a sample from a patient before the patient receives an intensification treatment with an HIV integrase inhibitor. The pre-intensification measurement may be made on or before the starting date of the intensification treatment, preferably on the starting date of the intensification treatment.

The term "post-intensification measurement" used herein refers to a measure of the concentration of an episomal artifact in a sample from a patient during or after the patient receives an intensification treatment with an HIV integrase inhibitor. The post-intensification measurement may be made on or after the starting date of the intensification treatment, and may be made daily, weekly, bi-weekly, monthly or bi-monthly, or on an irregular prescribed schedule, preferably weekly. The total number of post-intensification measurements may be 1, 2, 3, 4, 5, 6, 7, 8, 9, 10, or more, preferably 2. The post-intensification measurements may include a measurement of a peak concentration of the episomal artifact ($C_p$).

The samples used for pre- or post-intensification measurements are obtained from a patient, and may be of the same or different types, preferably the same type. The samples may comprise a cell, a tissue, a bodily fluid, or a combination thereof. The samples may be whole blood, lymph node biopsy, plasma, serum, saliva or urine. Preferably, the samples contain whole blood. The samples may contain peripheral-blood mononuclear cells (PBMCs) at, for example, at least about $10^6$, $10^7$ or $10^8$ PBMCs, preferably at least about $10^7$ PBMCs.

The term "pre-intensification HIV infection success ratio (R)" used herein is also known as the effective reproductive ratio (R), and refers to the average number of uninfected cells infected by an infected cell during its lifetime. Another related term is "the basic reproductive ratio ($R_0$)," which is the average number of uninfected cells infected by a single infected cell during its lifetime when target cells are assumed to be abundant. This quantity $R_0$ is always greater than 1 in untreated patients, allowing the establishment of infection. The goal of an antiviral treatment is to reduce this quantity $R_0$ below 1, resulting in exponential decline in infected cell populations. $R_0$ does not change with time, but it may change with experimental condition (i.e., treated vs. untreated) or anatomic location (as in a sanctuary site). If $R_0 > 1$, then R will initially equal $R_0$, but will decline as target cells are depleted. This will continue until the production of infected cells exactly equals the replenishment rate of target cells. At this equilibrium condition, R=1 if there are no other sources of infected cells, or slightly less than one if there are exogenous sources of infected cells. If $R_0 < 1$, then R will approximately be equal to $R_0$ for all time.

In the method according to the present invention, R is computed based on a series of measurements of episomal artifacts (C(t)), and their associated measurement times (t), for example, the pre- and post-intensification measurements of the episomal artifacts. One or more other values, measured or estimated, may also be used in computing R. Such other values may include a death rate of actively infected cells (a), a rate of production of actively infected cells by processes other than infection ($y_e$), ratio-reduction in R following the intensification ($\eta_{II}$), a ratio of the probability of the episomal artifact formation during an infection event when the HIV integrase inhibitor is not present to the probability of the episomal artifact formation when the HIV integrase inhibitor interrupts an infection event ($\varphi$), probability of the episomal artifact formation when the HIV integrase inhibitor interrupts an infection event ($k_{II}$), a decay rate of the episomal artifact ($\delta$), a post-intensification peak concentration of the episomal artifact ($C_p$), a concentration of peripheral blood mononuclear cells (PBMCs) in a whole blood sample ($PMBC_m$), an effective volume of the patient ($V_e$), one or more measurements of plasma viral load v(t), and the associated measurement times (t). Preferably, such other values may include a death rate of actively infected cells (a), a rate of production of actively infected cells by processes other than infection ($y_e$), ratio-reduction in R following the intensification ($\eta_{II}$), a ratio of the probability of the episomal artifact formation during an infection event when the HIV integrase inhibitor is not present to the probability of the episomal artifact formation when the HIV integrase inhibitor interrupts an infection event ($\varphi$), probability of the episomal artifact formation when the HIV integrase inhibitor interrupts an infection event ($k_{II}$), a decay rate of the episomal artifact ($\delta$), one or more measurements of plasma viral load v(t), and the associated measurement times (t).

The term "sufficiently close to 1" as used herein refers to a pre-intensification HIV infection success ratio (R) that is within ±10%, ±5%, ±1%, ±0.5%, ±0.1%, ±0.05%, ±0.01%, ±0.005% or ±0.001% of 1, preferably within ±5% of 1, more preferably within ±1% of 1, most preferably within ±0.1%. For example, a pre-intensification HIV infection success ratio (R) in the range from 0.9, 0.95 or 0.99 to 1 indicates that the patient has efficient cryptic HIV replication with an associated degree of certainty.

The results obtained from the method according the present invention may be used to assess the efficacy of a suppressive antiviral therapy received by a patient. The presence of efficient cryptic HIV replication in a patient may indicate that the patient has or will likely develop HIV mutants resistant to the suppressive antiviral therapy, and suggest modification of the suppressive antiviral therapy to prevent or minimize development of drug resistant HIV mutants in the patient. The results may also be used to guide modification of the suppressive antiviral therapy to improve its efficacy.

Where efficient cryptic HIV replication is detected in a patient, the efficient cryptic HIV replication may be quantified. In particular, the magnitude of a pre-intensification HIV infected-cell turnover rate (ay(0)) may be computed. For example, the computation is made based on the pre- and post-intensification measurements.

Based on the magnitude of the pre-intensification HIV infected-cell turnover rate (ay(0)) in a patient, the suppressive antiviral therapy received by the patient may be modified to improve its efficacy in the patient. The modification may involve changing one or more drugs in the suppressive antiviral therapy or adding one or more antiviral drugs to the suppressive antiviral therapy. The modification may consist of continuing the use of the integrase inhibitor intensification. The modification may also involve adjusting the dose of an antiviral drug in the therapy. The modification may lead to a reduction of the pre-intensification HIV infection success ratio (R) in the patient. After the modification, R may be reduced to less than about 0.99, 0.95, 0.9, 0.8, 0.7, 0.6, 0.5, 0.4, 0.3, 0.2 or 0.1, preferably less than about 0.8, more preferably less than about 0.6. The goal of such modification is to eliminate the presence of cryptic viremia. Success of the modified may be confirmed by a second detection of cryptic viremia by the methods described herein.

For each method according to the present invention, a system is provided. The system comprises one or multiple processors and a computer readable medium coupled to the processors, having instructions which when executed cause the at least one processor to carry out the computing steps in the method. Multiple processors may work in parallel. The computer readable medium may include data such as a series of measurements of episomal artifacts (C(t)), and their associated measurement times (t), for example, the pre- and post-intensification measurements of the concentration of an episomal artifact in one or more samples from a patient. The computer readable medium may also include data such as a death rate of actively infected cells (a), a rate of production of actively infected cells by processes other than infection ($y_e$), ratio-reduction in R following the intensification ($\eta_{II}$), a ratio of the probability of the episomal artifact formation during an infection event when the HIV integrase inhibitor is not present to the probability of the episomal artifact formation when the HIV integrase inhibitor interrupts an infection event ($\varphi$), probability of the episomal artifact formation when the HIV integrase inhibitor interrupts an infection event ($k_{II}$), a decay rate of the episomal artifact ($\delta$), a post-intensification peak concentration of the episomal artifact ($C_p$), a concentration of peripheral blood mononuclear cells (PBMCs) in a whole blood sample ($PMBC_m$), an effective volume of the patient ($V_e$), one or more measurements of plasma viral load v(t), and the associated measurement times (t). The computer readable medium may also include programs for computing a pre-intensification HIV infection success ratio (R) or the magnitude of a pre-intensification HIV infected-cell turnover rate (ay(0)). The system leads to detection of efficient cryptic HIV replication in a patient for various purposes.

A system for detecting efficient cryptic HIV replication in a patient is provided. The patient receives a suppressive antiviral therapy not containing an HIV integrase inhibitor followed by administration of the HIV integrase inhibitor in an effective amount for intensifying the suppressive antiviral therapy, and has undetectable plasma viremia prior to the administration of the HIV integrase inhibitor. The system comprises: a processor and a computer readable medium. The computer readable medium is coupled to the processor, and has instructions which when executed cause the processor to compute a pre-intensification HIV infection success ratio (R). R is computed based on a series of measurements of episomal artifacts (C(t)), and their associated measurement times (t), for example, (a) a pre-intensification measurement of the concentration of an episomal artifact in a pre-intensification sample from the patient, and (b) one or more post-intensification measurements of the concentration of the episomal artifact in one or more post-intensification samples from the patient. A pre-intensification HIV infection success ratio (R) sufficiently close to 1 indicates the presence of the efficient cryptic HIV replication in the patient.

In some embodiments, the system may further comprise a processor and a computer readable medium. The computer readable medium is coupled to the processor, and has instructions which when executed cause the processor to compute a pre-intensification HIV infected-cell turnover rate (ay(0)) based on the pre- and post-intensification measurements. The processor and the computer readable medium used to compute the pre-intensification HIV infected-cell turnover rate (ay(0)) may be the same as or different from those used to compute the pre-intensification HIV infection success ratio (R).

The system according to the present invention may also comprise a centralized computing server, and associated software to allow remote submission of measured patient data from testing sites, and remote reporting of computed pre-intensification HIV success ratio (R) and pre-intensification HIV infected-cell turnover rate (ay(0)) to the testing site. The system may also comprise a centralized computing server as described above, where the remote submission and remote reporting is carried out using encrypted or secure methods.

The term "about" as used herein, when referring to a measurable value such as an amount, a percentage, and the like, is meant to encompass variations of ±20%, +10%, more preferably ±5%, even more preferably ±1%, and still more preferably ±0.1% from the specified value, as such variations are appropriate.

Example 1. Detecting and Quantifying Cryptic HIV Replication from Measured 2-LTR Dynamics Following Raltegravir Intensification 1. Introduction In a recently published INTEGRAL study, 45 patients on HAART who had maintained plasma viremia undetectable by standard assays for at least 1 year received standard HAART intensified by the addition of raltegravir for 48 weeks. During this time, Peripheral-Blood Mononuclear Cell (PBMC) samples were analyzed for the presence of cells containing 2-LTR circles. 2-LTR circles are formed when the linear viral DNA is prevented from integrating into the host cell genome, either through failed integration or through the action of integrase inhibitors such as raltegravir. It is expected, therefore, that the numbers of 2-LTR containing cells would increase if the raltegravir was interrupting otherwise successful infection events. 2-LTR containing cells were observed in 13/45 patients receiving raltegravir intensification, compared to 1/22 patients in the control group; this was interpreted as indicating de novo infection and reverse transcription, which strongly suggests that active viral replication persists despite HAART in these individuals.

In this study, we further analyze this data through the use of a mathematical model of 2-LTR formation during virus replication. Analysis of this model shows that increase in 2-LTR containing cells is not, by itself, evidence of significant levels of ongoing replication. Instead, the model shows that rapid increase followed by a decrease in 2-LTR cells is evidence of significant levels of ongoing infection, while a moderate monotonic increase in 2-LTR cells would be consistent with low levels of ongoing infection.

Intuitively, this is because when there is very little ongoing replication, raltegravir intensification will increase the rate of 2-LTR formation, but will not significantly decrease the number of infection events, as the success rate of infection events was already very low. As a result, we would expect to see a sustained increase in 2-LTR count in this case. Conversely, if there is a significant amount of ongoing replication, raltegravir intensification will increase the rate of 2-LTR infection, but it will also significantly decrease the success rate of infection events. In this case, we expect an initial spike in 2-LTR count, followed by a drop in 2-LTR count as the raltegravir dramatically decreases the incidence of new infection events. This second case is what was seen experimentally in the clinical trial.

When analyzed using this model, it becomes clear that the data from 7 patients in the INTEGRAL study are consistent with significant levels of ongoing efficient ($R_0 > 1$) viral replication in a sanctuary site prior to raltegravir intensification. Median estimates of the infected cell turnover rate for these 7 patients range from 10 million to 310 million infected cells per day. This ongoing replication rate may be high enough to allow for evolution of resistant virus. The number of patients in the study, however, is insufficient to determine whether these levels of viral replication are typical of HIV patients under effective suppressive therapy, or if they are an anomaly.

2 Materials and Methods 2.1 Experimental Methods

Ethics Statement

The previously published clinical study was carried out in accordance with a human subjects protocol approved by the institutional ethics review committee at each clinical site. Written informed consent was obtained from all study participants. Patient data was shared in de-identified form in accordance with a protocol approved by the University of Delaware Institutional Review Board.

Study Design

This study uses data from a previously published study. The 2-LTR measurement results which are the focus of this work have been previously described in References 36 and 37. Briefly, a three-site clinical study performed in Barcelona (Spain) enrolled 69 HIV seropositive patients on suppressive HAART regimens with undetectable viremia for at least 1 year prior to the study. Informed consent was obtained from all study subjects. Twenty-four were randomized to a control group which continued standard HAART, and 45 to a treatment group which continued HAART with the intensification of raltegravir. An average of $6 \times 10^7$ PBMC were sampled and purified from all patients at weeks 0, 2, 4, 12, 24 and 48. The number of HIV 2-LTR circles in these samples were quantified using single-step real-time PCR. 2-LTR circles were detected in 13 of the 45 patients in the experimental group; the data from these 13 patients is used in this study, and is shown as reported in References 36 and 37 in Table 1, corrected for a theoretical censoring limits.

2.2 Modeling 2-LTR Formation Following Raltegravir Intensification

Previous work has been done on identifying HIV model parameters from experiments involving the use of integrase inhibitors. These models, however, considered only standard viral load measurements, not measurements of 2-LTR circle frequency. We introduce a simple model of the dynamics of the concentrations of actively infected cells y(t) and cells containing 2-LTR episomes c(t) in the site of episome formation. We model the behavior both in the absence of raltegravir $u_{II}=0$ and in the presence of raltegravir $u_{II}=1$.

We consider two possible sources of active compartment infected cells: de novo replication events that are inhibited by raltegravir, and exogenous sources of infected cells that are unaffected by raltegravir ($y_e$). This exogenous source includes the activation of quiescent infected cells, but may also include any source of efficient de novo replication which is not suppressed by the addition of raltegravir.

The reproductive ratio of the virus prior to raltegravir intensification is R, and the reproductive ratio after raltegravir intensification is $(1-\eta_{II})R$, where $\eta_{II}$ is the effectiveness of raltegravir at interrupting infection events that would otherwise have occurred without intensification. The reproductive ratios are defined as the average number of infected cells created per infected cell in a single generation. If the virus was replicating efficiently prior to intensification ($R_0 > 1$), then the measured R would be approximately equal to 1 at equilibrium, as the efficient replication would necessarily be target cell limited. If the infection is controlled prior to intensification ($R_0<1$), then the measured reproductive ratio R will be approximately equal to $R_0$.

Infected cells are killed by the virus at a rate ay. Successful infection of target cells by free virus occurs at a rate aRy prior to intensification or at a rate $(1-\eta_{II})$Ray post-intensification. Intrinsic formation of 2-LTR cells (unenhanced by raltegravir) is assumed to occur at a rate proportional to the successful infection rate, with a proportionality constant of $\varphi k_{II}$. This is the rate of formation in all cells prior to intensification, and the rate of formation in the cells unaffected by raltegravir following intensification. Intrinsic formation therefore occurs prior to intensification at a rate $\varphi k_{II}$Ray, and post-intensification at a rate $\varphi k_{II}(1-\eta_{II})$Ray.

2-LTR circles may also be formed at an integrase inhibitor-enhanced rate in the presence of raltegravir. The rate at which infection events are interrupted by raltegravir after intensification is $\eta_{II}$Ray which, when multiplied by the probability $0<k_{II}<1$ that the interruption of an infection even leads to the formation of a 2-LTR episome, gives us the rate of integrase inhibitor-enhances 2-LTR formation $k_{II}\eta_{II}$Ray. $\varphi \geq 0$ is the ratio between the intrinsic rate and the raltegravir-enhanced rate of 2-LTR formation.

Cells containing 2-LTR circles decay at a rate $\delta c$; the model does not distinguish whether this is due to death of the cell or decay of episomal DNA. These dynamics can be written in the form of Equation 1:

$$\dot{y} = -(1-(1-\eta_{II}u_{II})R)ay + y_e$$

$$\dot{c} = \varphi k_{II}(1-\eta_{II}u_{II})Ray + k_{II}\eta_{II}u_{II}Ray - \delta c \quad (1)$$

This is the simplest form in which the expected 2-LTR dynamics can be written, but it is also the correct simplification of the dynamics illustrated in FIG. 1 if it is assumed that the target cell concentrations are approximately constant and that free virus has a relatively short half-life. The intermediate steps of entry, reverse-transcription, and integration are considered to be part of the life-cycle of the infected cells y. If the exogenous sources of infected cells are non-zero, then by definition R<1 at equilibrium. Assuming that the dynamics have reached equilibrium prior to raltegravir intensification, the measured concentration of 2-LTR after raltegravir intensification is described by Equation 2

$$c(t) = c(\infty) + (c(0) - c(\infty))e^{-\delta t} + \quad (2)$$
$$c(\infty)\frac{\delta \eta_{II} R}{(1-R)(\alpha(1-(1-\eta_{II})R)-\delta)}(e^{-\delta t} - e^{-\alpha(1-(1-\eta_{II})R)t})$$

with initial and final values:

$$c(0) = \frac{k_{II} y_e \phi R}{\delta(1-R)} \quad (3)$$

$$c(\infty) = \frac{k_{II} y_e R(\phi + \eta_{II} - \phi \eta_{II})}{\delta(1-(1-\eta_{II})R)}$$

Figure 2:
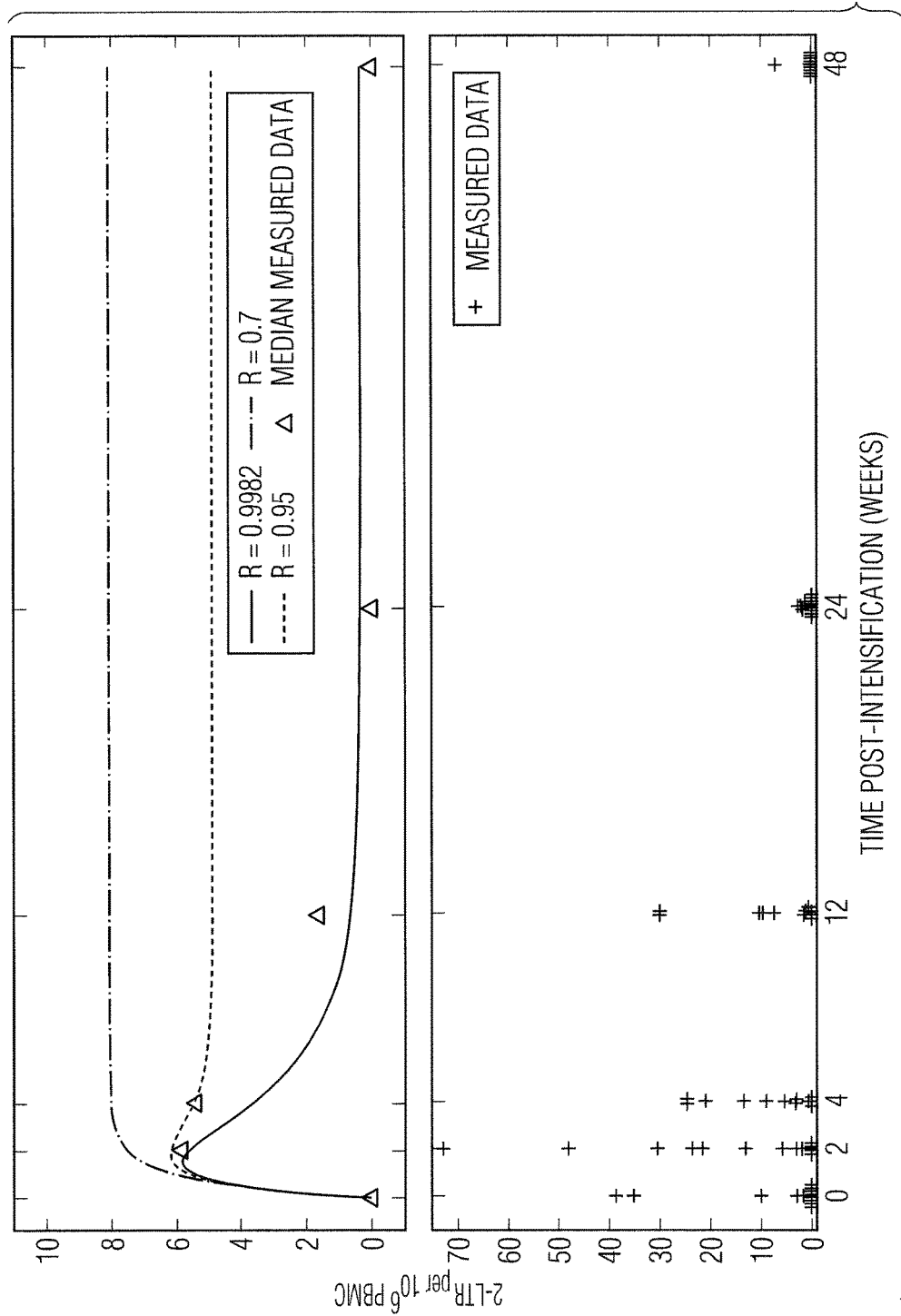
FIG. 2 shows 2-LTR responses predicted by the model for varying effective reproduction rates. Either with efficient viral replication (R=0.9982) (bottom curve in top panel), intermediate viral replication (R=0.95) (middle curve in top panel) or with little ongoing viral replication (R=0.7) (top curve in top panel). $y_e$ is scaled to provide identical levels of pre-intensification turnover. The median measured data and the measured data points are shown for comparison.

The expected 2-LTR concentrations following raltegravir intensification are shown in FIG. 2, both for the case of controlled replication prior to intensification and for efficient replication prior to intensification. This model is consistent with both the experimental and null hypothesis, as defined in the next section.

2.2.1 Bounds on R

The fact that the total virus load is contained prior to the experiment implies that R<1. We can show that both monotonic decrease in 2-LTR circles as well as an increase followed by a decrease following raltegravir intensification can only be explained by R being close to 1 before intensification. Consider that:

$$c(0) > c(\infty) \Longrightarrow R + \varphi > 1$$
$$c(0) < c(\infty) \Longrightarrow R + \varphi < 1 \quad (4)$$

For the values of $\varphi$ suggested by the experiments in References 40 and 41, this would suggest a lower bound on R>0.95 for all patients for which the initial value c(0) is greater than the final value $c(\infty)$. From the experimental data in Table 2, this is true for patients 001-33, 001-43, 001-44, 006-69, and 023-68.

Consider that $c(t) = c_H(t) + c_F(t)$, where $$C_H(t) = c(\infty) + (c(0) - c(\infty))e^{-\delta t} \quad (5)$$

$$c_F(t) = c(\infty)\frac{\delta(R - (1-\eta_{II})R)}{(1-R)(\alpha(1-(1-\eta_{II})R)-\delta)}(e^{-\delta t} - e^{-\alpha(1-(1-\eta_{II})R)t})$$

Let tp be the time at which c(t) reaches a maximum. $c_H(t)$ is a monotonic transition from initial to final value, so:

$$\min\{c(0), c(\infty)\} \leq c_H(t) \leq \max\{c(0), c(\infty)\} \quad (6)$$

Solving for the maximum value of $C_F(t)$, we find $$0 \leq c_F \leq c(\infty)\frac{(R(1-\eta_{II})R)}{(1-R)}\left(\frac{\alpha(1-(1-\eta_{II})R)}{\delta}\right)^{\frac{-\delta}{\alpha(1-(1-\eta_{II})R)-\delta}} \leq \quad (7)$$
$$c(\infty)\frac{(R-(1-\eta_{II})R)}{(1-R)}$$

so $$c(t_p) = c_H(t_p) + c_F(t_p) \leq \max\{c(0), c(\infty)\} + c(\infty)\frac{(R-)1-\eta_{II})R)}{(1-R)} \quad (8)$$

This leads to conservative bounds on R based on the peak value of $c(t_p)$:

$$\frac{c(t_p) - \max\{c(0), c(\infty)\} + c(\infty)(1-\eta_{II})R}{c(t_p) - \max\{c(0), c(\infty)\} + c(\infty)} \leq R \leq 1 \quad (9)$$

Assuming that $(1-\eta_{II})R=0$, results in the very conservative lower limit:

$$\frac{c(t_p) - \max\{c(0), c(\infty)\}}{c(t_p) - \max\{c(0), c(\infty)\} + c(\infty)} \leq R \leq 1 \quad (10)$$

2.3 Hypotheses

The null hypothesis H0 is the hypothesis that the addition of raltegravir does not affect the dynamics of 2-LTR formation. In our model, this is equivalent to setting $\eta_{II}=0$, which would lead to the solution following intensification of $c(t)=c(0)$. This hypothesis has one degree of freedom per patient, which is the constant, average measured value of 2-LTR circles, for a total of 13 degrees of freedom.

$H_1$

The experimental hypothesis $H_1$ is that the addition of raltegravir does affect the dynamics of 2-LTR formation, which follow the dynamics of Equation 5. We assume that the decay rate of 2-LTR containing cells 6 and the ratio of intrinsic to integrase inhibitor enhanced 2-LTR formation φ do not vary significantly from patient to patient, while the reproductive ratio R, the raltegravir efficacy $\eta_{II}$, and the scaled exogenous infected cell rate $k_{II}y_e$ may vary significantly from patient to patient, giving us a total of 41 degrees of freedom for the experimental hypothesis.

2.4 Relationship to Previously Published Models

To show that this reduced model is consistent with previously published models of virus dynamics, we introduce an adaptation of the standard model of HIV dynamics that accounts for the formation of 2-LTR cells in the presence and absence of the integrase inhibitor raltegravir, assuming the patient is already on an apparently effective antiviral regimen. The model takes the form of Equation 11

$$\dot{x} = \lambda - dx - \beta^*(1-\eta_{II}u_{II})xv$$

$$\dot{y} = \beta^*(1-\eta_{II}u_{II})xv - ay + y_e$$

$$\dot{v} = \gamma y - \omega v$$

$$\dot{c} = \beta^* xv(\varphi k_{II}(1-\eta_{II}u_{II}) + k_{II}\eta_{II}u_{II}) - \delta_c \quad (11)$$

where x is the local concentration of target cells, y is the local concentration of actively infected cells, v is the local concentration of free virus, and c is the local concentration of cells containing 2-LTR episomes. As in the standard model, λ is the regeneration rate of target cells, d is the per-capita death rate of target cells, β* is the infection rate constant of target cells, corrected for the activity of the pre-intensification antiviral regimen, a is the per-capita death rate of actively infected cells, γ is the per-capita production rate of free virus by actively infected cells, and ω is the per-capita decay rate of free virus. A more extensive model of virus dynamics in the presence of raltegravir, including the intermediate events before integration, is presented in Reference 43.

The efficacy of raltegravir at further inhibiting infection events is r, and the input $u_{II}$ takes a value of 0 or 1 depending on whether raltegravir is being applied. If a virus entry event is not interrupted by raltegravir, there is a small probability $\varphi k_{II}$ that the virus entry event will result in an aborted infection and the formation of a 2-LTR episome. The rate at which virus entry events occur is assumed to be proportional to the successful infection rate β*xv. The addition of raltegravir interferes with the infection process with an efficacy $\eta_{II}$; the cells which are prevented from successful infection are assumed to form 2-LTR episomes at a much higher probability $k_{II}$. The cells containing 2-LTR decay at a rate δ.

Actively infected cells are created by exogenous processes (including activation of quiescent infected cells) at a rate $y_e$.

If the activity of the existing antivirals in the site is sufficient to contain the virus (i.e., the basic reproductive ratio $$R_0 = \frac{\beta * \lambda \gamma}{d a \omega} < 1,$$

then the target cell concentrations will remain very close to the virus-free equilibrium $$\frac{\lambda}{d}.$$

Assuming also that the ω>>a the virus dynamics reduce to the linear form:

$$\dot{y} = \alpha \frac{\beta^* \lambda \gamma}{d a \omega}(1 - \eta_{II}u_{II})y - \alpha y + y_e \quad (12)$$

$$\dot{c} = \alpha \frac{\beta^* \lambda \gamma}{d a \omega} y(\varphi k_{II}(1-\eta_{II}u_{II}) + k_{II}\eta_{II}u_{II}) - \delta c$$

which is exactly the form of Equation 1, with $R=R_0$.

2.5 Relationship to Spatial Models

When the local activity of the antivirals is sufficiently weak that $$R_0 = \frac{\beta^* \lambda \gamma}{d a \omega} > 1,$$

then the model describes the target-cell limited replication of the virus in a sanctuary site. The dynamics have been explored numerically for a spatially discretized reaction-diffusion Partial Differential Equation model in Reference 44. The results are summarized below:

2.5.1 Model

Biological Background

When viral cDNA fails to integrate into host CD4+ T cells, episomal artifacts including linear unintegrated DNA, 1-LTR circles, and 2-LTR circles form. This can only happen following a successful reverse transcription event. Previous studies have shown no significant viral change in the blood after raltegravir intensification in patients under HAART. If the 2-LTR production is arising from interrupted rounds of successful infection, this implies that the 2-LTR containing T-cells come from an anatomical compartment diffusively remote from the blood. The model we propose assumes that the paracortex/follicle within lymph nodes are anatomical compartments with reduced drug efficacy, from which T-cells with 2-LTR recirculate after raltegravir is applied. The main objective is to determine whether this hypothesis is consistent with the observed dynamics of 2-LTR following raltegravir intensification.

The re-circulation and motility of T-cells has been broadly studied. Re-circulation includes the entry into the lymph node, the motility inside and the exit from the paracortex of the node. There are two main entries for lymphocytes into the lymph nodes, through high endothelial venules (HEV) and the afferent lymphatic vessels (AL) in the subcapsular sinus. The HEV route is preferred over the AL for T-cells so that in the absence of infection, up to ~2 percent of T-cells are recruited via HEVs from the recirculating pool per day. This preferred way for T-Cells to enter the lymph nodes is highly selective and efficient. A guided cascade facilitates the crossing of the lymphocytes through the HEV's wall. Inside the paracortex of the lymph node, the cells follow a random walk in a cord-like arrangement of concentric layers of fibroblastic reticular cells (FRCs). Each paracortical cord is between 10 and 15 μm in length, and the T-cells has been reported to have an average 3D velocity of ~15 μm/min and a motility coefficient about 50-100 μm$^2$/min. The random walk permits the interaction of T-cells with dendritic cells needed to recognize antigens. If naive lymphocytes do not encounter antigens, they eventually leave the paracortex by the cortical sinus and the lymph node through efferent lymphatics.

Several different approaches have been used to model lymph nodes, but none with the purpose of explaining ongoing viral replication. Some researchers have explained HIV dynamics in compartments but none have accounted for 2-LTR formation as a marker of low level replication. In this work, we model the viral dynamics in the blood and the in lymph nodes paracortex/follicle sites, including the transport of cells and virus between them. We show that the observed patterns of 2-LTR dynamics following raltegravir intensification can be reproduced by our model if and only if the sanctuary sites are sufficiently large and the drug efficacy within the sites is sufficiently small. We show that, in the absence of these conditions, fundamentally different patterns of measured 2-LTR in the blood are predicted following raltegravir intensification.

Mathematical Model

The model represents the conditions for the formation of 2-LTR in T-cells due to HIV dynamics both inside the lymphoid follicles and the blood as well as the motility of the CD4+ T cells among them. We used the well-known Nowak viral dynamics model of HIV dynamics with its assumptions. Furthermore, we include the assumptions that the two sources of 2-LTR formation in T-cells are the intrinsic one unenhanced by raltegravir and the one caused by the application of raltegravir formulated in Reference 55 and used in Reference 44. Several assumptions of the recirculation and motility of the T-cells and HIV in the initial compartmental model are proposed in Reference 44. Firstly, the recirculation of T-cells from the inner sites of the lymph nodes to the lymphatic vessels and the blood is diffusion-like. Second, the motility of T-cells inside the lymphoid follicles is also analogous to diffusion, moving in apparently random walk fashion. Third, HIV is only transported in/out the lymphoid follicles inside infected T-cells. Fourth, HIV moves inside the lymphoid follicles by diffusion. Fifth, the Lymphoid Follicle is well-described by concentric homogenous spherical-shell domains. Finally, we assume the blood and lymphatic vessels can be jointly described by a single, well-stirred compartment.

Figure 4:
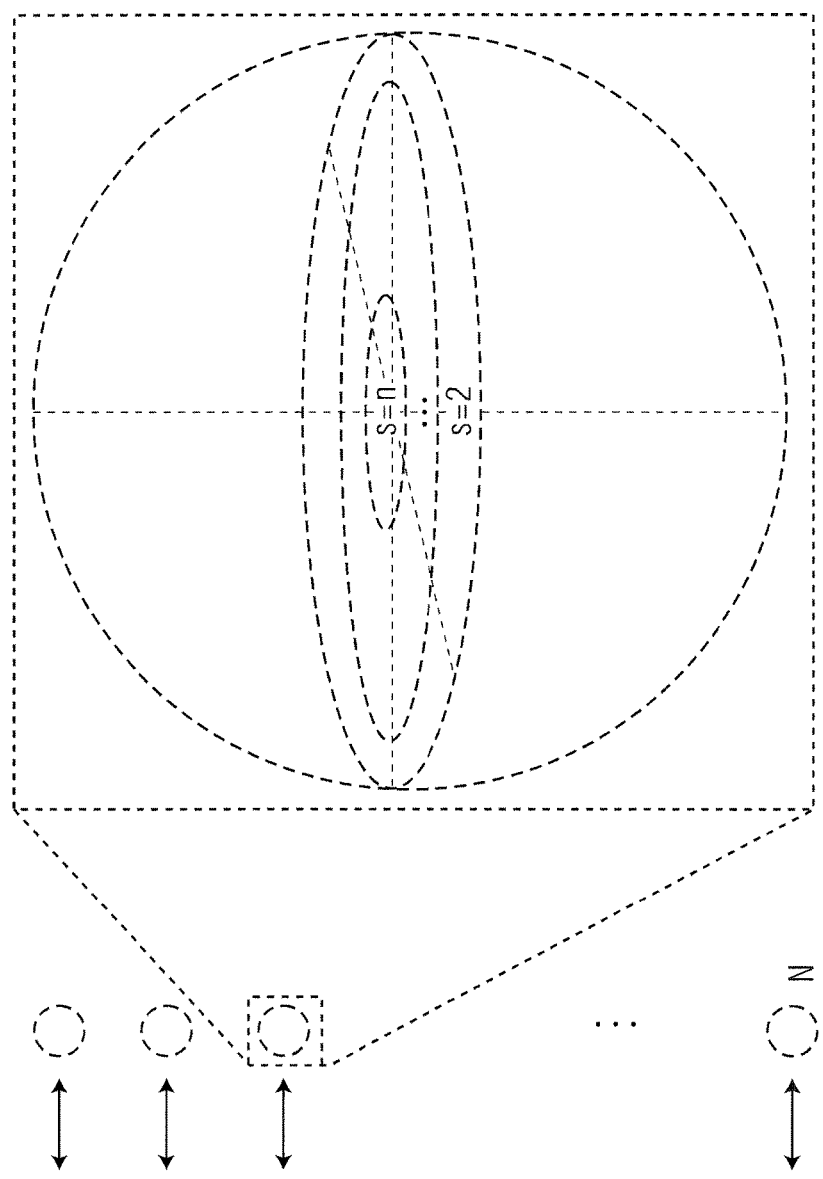
FIG. 4 illustrates configuration of compartments, on the left part the main compartment representing the blood, HEVs and lymphatic vessels, in the middle the N secondary spherical compartments representing the lymph nodes paracortex/follicle sites, and on the right the formulation of each sphere as n−1 concentric homogenous shells.

Based on these assumptions, we simplify the reaction-diffusion equations describing the dynamics into a set of compartmental diffusively-coupled ODEs with the following configuration: one main compartment representing the blood, the HEVs and the lymphatic vessels and N secondary compartments representing all the lymph nodes paracortex/follicle sites in human body. These N compartments have no connections between them but only with the main compartment as FIG. 4 depicts. Each of the N secondary spherical compartments is assumed to be subdivided into $n-1$ concentric spheres where only the most external one is connected with the blood compartment. Since all N compartments have the same geometrical configuration, we use an ODE model of $4n$ equations with the first compartment having the form, $$\dot{x}_1 = \lambda - dx_1 - \quad (13)$$

$$\beta x_1 v_1 (1 - \eta_{RTI} u_{RTI} \theta_1)(1 - \eta_{II} u_{II} \xi_1) + N \frac{D_{x1,2}}{l} \frac{A_{1,2}}{V_1}(x_2 - x_1)$$

$$\dot{y}_1 = \beta x_1 v_1 (1 - \eta_{RTI} u_{RTI} \theta_1)(1 - \eta_{II} u_{II} \xi_1) -$$

$$\alpha y_1 + y_e + N \frac{D_{y1,2}}{l} \frac{A_{1,2}}{V_1}(y_2 - y_1)$$

$$\dot{v}_1 = \gamma(1 - \eta_{PI} u_{PI} \varphi_1)y_1 - \omega v_1 + N \frac{D_{v1,2}}{l} \frac{A_{1,2}}{V_1}(v_2 - v_1)$$

$$\dot{c}_1 = \beta x_1 v_1 (1 - \eta_{RTI} u_{RTI} \theta_1)(k_{INT}(1 - \eta_{II} u_{II} \xi_1) + k_{II} \eta_{II} \xi_1) -$$

$$\delta c_1 N \frac{D_{c1,2}}{l} \frac{A_{1,2}}{V_1}(c_2 - c_1),$$

where $A_{1,2}$ represents the surface area of the paracortex/follicle site in the lymph node, $V_1$ represents the volume of the main compartment and $$\frac{D_{xi,s}}{l} = \frac{D_{yi,s}}{l} = \frac{D_{ci,s}}{l} \text{ and } \frac{D_{vi,s}}{l}$$

represents the effective diffusivity of T-Cells and HIV virions between the main compartment and the paracortex/follicle site. Furthermore, for each concentric layer $s = 2, \ldots, n$, of each of the N compartments have the form, $$\dot{x}_s = \lambda - dx_s - \quad (14)$$

$$\beta x_s v_s (1 - \eta_{RTI} u_{RTI} \theta_s)(1 - \eta_{II} u_{II} \xi_s) + \Sigma_{i \neq s} \frac{D_{xi,s}}{l} \frac{A_{i,s}}{V_s}(x_i - x_s)$$

$$\dot{y}_s = \beta x_s v_s (1 - \eta_{RTI} u_{RTI} \theta_s)(1 - \eta_{II} u_{II} \xi_s) -$$

$$\alpha y_s + y_e + \Sigma_{i \neq s} \frac{D_{yi,s}}{l} \frac{A_{i,s}}{V_s}(y_i - y_s)$$

$$\dot{v}_s = \gamma(1 - \eta_{PI} u_{PI} \varphi_s)y_s - \omega v_s + \Sigma_{i \neq s} \frac{D_{vi,s}}{l} \frac{A_{i,s}}{V_s}(v_i - v_s)$$

$$\dot{c}_s = \beta x_s v_s (1 - \eta_{RTI} u_{RTI} \theta_s)(k_{INT}(1 - \eta_{II} u_{II} \xi_s) + k_{II} \eta_{II} \xi_s) -$$

$$\delta c_s + \Sigma_{i \neq s} \frac{D_{ei,s}}{l} \frac{A_{i,s}}{V_s}(c_i - c_s),$$

where $A_{i,s}$ represents the surface area between each layer in the sphere, $V_s$ represent the volume of the layer, and $$\frac{D_{xi,s}}{l} = \frac{D_{yi,s}}{l} = \frac{D_{ci,s}}{l} \text{ and } \frac{D_{vi,s}}{l}$$

represents the effective diffusivity of T-Cells and HIV virions between layers.

As depicted in FIG. 1, in each compartment CD4+T target cells $x_s$, are produced at a rate $\lambda$, decay at a rate $dx_s$ and are infected at a rate $\beta x_s v_s$. The rate is reduced by the activity of reverse transcriptase inhibitors (RTI) $u_{RTI}$ and integrase inhibitors (II) $u_{II}$ with maximum effectiveness of $\eta_{RTI}$ and $\eta_{II}$. We hypothesize that the efficacy of the drug depends on the domain; therefore, we include a spatial dependence drug penetration distribution $\theta_s$ and $\xi_s$ for RTI and II respectively. Exogenous sources, particularly the activation of latent infected T-cells, contribute to create actively infected cells at a rate $y_e$. The infected cells $y_s$ die at a rate $\alpha y_s$ and produce virions at a rate $\gamma y_s$. This viral production is interrupted by protease inhibitors $u_{PI}$ with maximum efficiency $\eta_{PI}$ (the activity of protease inhibitors results in the production of non-infectious particles, which are neglected in this model). The activity of this drug is also assumed to vary spatially by a factor $\varphi_s$. Free virus exponentially decays at a rate $\omega v_s$. Viral entry leads to the formation of linear unintegrated HIV DNA at a rate inhibited by the activity of RTI drugs. In the case of no integrase inhibitor intensification ($u_{II}=0$), DNA copies may fail to integrate into the host cell genome at a small intrinsic rate $k_{INT}$ resulting in the formation of cells with 2-LTR $c_s$. In the case of intensification with integrase inhibitors ($u_{II}=1$), this rate of 2-LTR production is increased to $k_{II} \eta_{II} u_{II} \xi_s$ in this compartment, with a concomitant decrease in the intrinsic rate to avoid the possibility of counting the same 2-LTR formation event twice. The 2-LTR containing cells decay at a rate $\delta c_s$.

2.5.2 Parameters

To obtain realistic conditions for the 2-LTR dynamics observed in blood assuming lymph nodes paracortex/follicle acting as sanctuary sites, the parameters for viral dynamics, 2-LTR formation, drug penetration, and diffusion/geometry values have to be defined. The parameters include the local reaction rates and the diffusion rates between compartments.

HIV Reaction Rates.

For viral dynamic parameters, we use the values obtained by parameter identification in Reference 56 generated by a Bayesian Markov-Chain Monte Carlo technique. This study estimates the parameters from data taken from HIV patients who had 3 to 5 treatment interruptions cycles each. These data produced a posterior distribution of parameter values, including drug efficacy, conditioned on the observed data. Table 5 shows the parameter ranges used in this study.

2-LTR Formation Rates.

The parameters for the 2-LTR formation include $K_{II}$, $K_{INT}$, and $\delta$. $K_{II}$ and $K_{INT}$ are the product of a scaling factor which describes the volume that contains $10^6$ PBMC (Peripheral Blood Mononuclear cells) and non-dimensional factors that relate the fraction of integration events that fail after raltegravir is applied and before application, respectively. $\delta$ is the decay rate of observed 2-LTR in vivo. Shown in Table 6 are the maximum likelihood estimation for $\delta$ and confidence intervals for $K_{II}$ and $K_{INT}$ obtained in Reference 55 using data from Reference 36 and the values estimated from previous studies.

Diffusion.

The diffusion parameters in the model depend on the diameter of the spherical compartment and the values for effective diffusivity of the T-cells and the virus. Studies have shown that hyperplastic lymphoid follicles can be as large as 1 mm in diameter. Thus, we set the site diameter between 0.5 to 2 mm to determine the effect site size has on the 2-LTR transient behavior.

To estimate the effective diffusivity of T-cells between the main compartment and the paracortex/follicle site $$\frac{D_{x1.2}}{l}, \frac{D_{y1.2}}{l} \text{ and } \frac{D_{c1.2}}{l}$$

we note that without infection, one mouse lymph node recruits approximately 2% of the T-cells from recirculating pool per day, and the average diameter of a mouse LN is 1 mm. Diffusion into the lymph node is given by the equation $$\frac{D_{x_b,LN}}{l} \frac{A_{b,LN}}{V_{LN}} x_b = 0.02 x_b,$$

where $$\frac{D_{x_b,LN}}{l}$$

is the effective diffusivity between the blood an one mouse lymph node, and $A_{b,LN}$ and $V_{LN}$ the surface area and volume of the mouse lymph node. Thus, $$\frac{D_{x_b,LN}}{l}$$

must be approximately 1/300 mm/day, which we use as the estimated value of $$\frac{D_{x1.2}}{l}, \frac{D_{y1.2}}{l} \text{ and } \frac{D_{c1.2}}{l}.$$

The effective diffusion of T-cells between layers within the lymphoid paracotex/follicle is the average value of the experimentally observed motility coefficient of T-Cells within lymphoid follicles of 0.1 mm²/day divided by the length of each layer $$l = \frac{r}{n-1},$$

where r is the radius of the paracortex/follicle site.

The effective diffusion of the virus approximately is assumed to be zero between the main compartment and the spherical sites and that the virus is carried into them only by T-cells. This is because the separating boundary is known to act as a molecular sieve for particles smaller than an HIV virus. The effective diffusivity between compartments is assumed to follow the derivation in References 60 and 61 for a spherical virus. Assuming the diameter of HIV equal to 120 nm a diffusion coefficient of 0.43 mm²/day is calculated and divided by the width of each layer, $$l = \frac{r}{n-1}$$

to obtain the effective diffusivity.

Sanctuary Sites and Drug Efficacy.

The drug penetration distribution in each compartment is not well understood, and we investigate multiple possibilities. If the compartments were isolated, then prior to integrase inhibitor application each compartment has a basic reproductive ratio, $$\hat{R}_{0_a} = \frac{\beta \lambda \gamma}{d\alpha} \times (1 - \eta_{RTI} u_{RTI} \theta_s) \times (1 - \eta_{PI} u_{PI} \varphi_s). \tag{15}$$

When the system reaches equilibrium and integrase inhibitor intensification $u_{II}$ is applied, each compartment has a basic reproductive ratio $\check{R}_{0_e}$ with the form $$\check{R}_{0_e} = \hat{R}_{0_s} \times (1 - \eta_{II} u_{II} \xi_s) \tag{16}$$

Note that the smaller the values of $\theta_s$, $\varphi_s$ or $\zeta_s$, the larger the initial growth rate of the virus in the compartment. We assume that each drug has a penetration of 100% in the first compartment, and for $\theta_s$ and $\varphi_s$ we assume a geometric sequence with ratio 1/2 while for $\zeta_s$ a geometric ratio equal to 1 and has a value of 0.7 for compartment 1 to n. Since we assume 100% penetration in compartment 1, $\hat{R}_{0_1}<1$ is guaranteed. Consequently, the region between the third and the $n^{th}$ compartment composes the true sanctuary site, with drug efficacy sufficiently low to enable persistent virus replication. The region diffusively furthest from the plasma has the smallest drug efficacy. This last compartment has an extremely low drug efficacy and $\hat{R}_{0_q}>1$. The second compartment composes a transition region, with reduced drug efficacy relative to the main compartment and $\hat{R}_{0_2} \sim 1$.

2.5.3 Monte-Carlo Simulation

Based on the models of equations (13) and (14), two Monte-Carlo simulations characterize the conditions under which the 2-LTR transient behavior (the initial rise follow by a fall of the episomes) is possible, subject to random variation of the HIV reaction and diffusion parameters within the prior distributions described in Tables 1 and 2. The first simulation seeks to determine the minimum value of $\hat{R}_{O_2}$ for which the 2-LTR transient behavior in blood is observed. Using the results of the first simulation, the second examines the change in the transient peak value of 2-LTR in the blood as the total tissue volume of the N compartments and the individual sphere diameter of lymph nodes varies.

$\hat{R}_{O_s}$ defines the reproductive ratio of the virus in compartment s prior to raltegravir intensification if the compartment were isolated (as the compartments are not isolated, the actual reproductive ratio can be greater or smaller depending on the behavior of neighboring compartments). When the value is greater than 1 the virus grows exponentially, and when smaller than 1 the virus decays exponentially. Since the drug distribution is assumed to decrease with compartment, the s=2 compartment has the highest drug activity in the sphere and thus the smallest $R_{O_e}$. Consequently, if there is viral replication in compartment s=2, this implies the presence of viral replication in all compartments s>2. Given this, we can use $\hat{R}_{O_2}$ as a measure to determine lower bound conditions for cryptic viremia under HAART before intensification and for 2-LTR transient results after intensification. To that end a 1000-trial Monte-Carlo simulation of the model defined by Equations (13) and (14) is run using parameters drawn from the prior distributions described above with values of $\hat{R}_{O_2}$ in the range 0.8 to 1.15 for and a total volume of spherical site tissue of 30 mL, with each individual site having diameters of either 0.5, 1, 1.5 or 2 mm. Note that, we are using a fixed tissue volume for the N spherical lymph nodes and for each change in an individual sphere, consequently the total number of spherical compartments N is variable. The median observed viral loads in the center of the spherical site (compartment 10) prior to integrase inhibitor intensification are plotted against $\hat{R}_{O_2}$ in FIG. 6.

Figure 5:
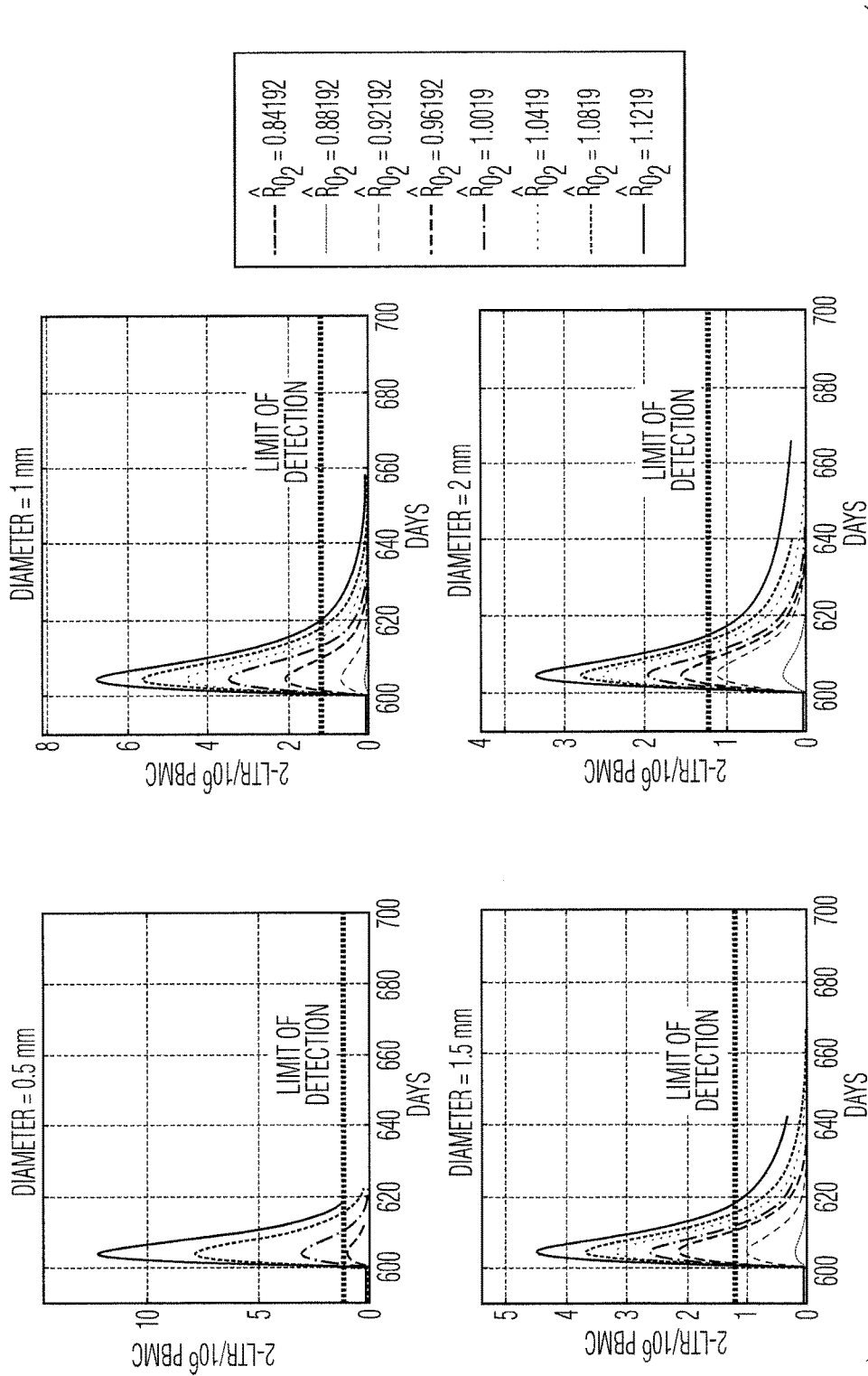
FIG. 5 shows average 2-LTR containing cells in the main compartment for a fixed total compartment volume. For diameter length 1, 1.5 and 2 mm the lower $\hat{R}_{O_2}$ bound for detectable peaks approximately over 0.96, and for the smaller case, diameter equal to 0.5 mm, the lower bound is $\hat{R}_{O_2} > 1$.
Figure 6:
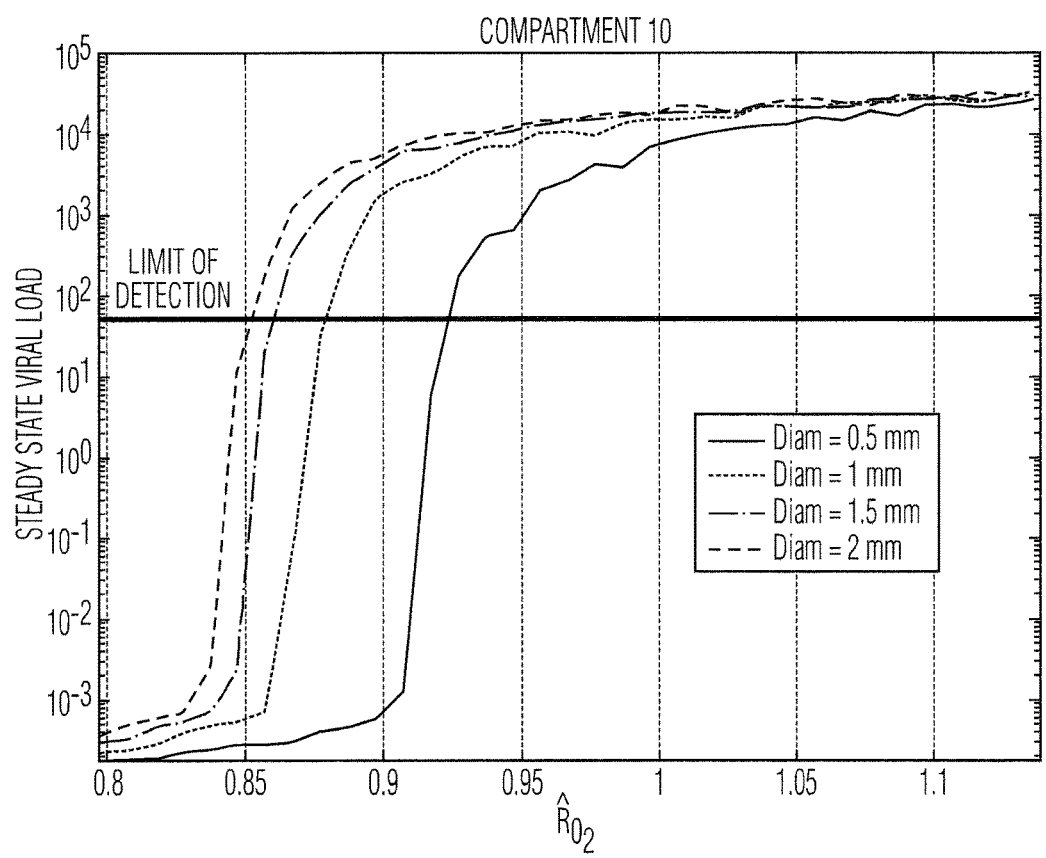
FIG. 6 shows average steady state of viral load in the most remote compartment versus $\hat{R}_{O_2}$ for diameter length of 0.5, 1, 1.5 and 2 mm.

The plot describes the median steady state viral load in compartment 10 before intensification and the horizontal line the normal assays limit of detection. In all cases, the viral load in Compartment 1, which describes the blood and free-owing lymph, was well below the limit of detection, demonstrating that the model is consistent with cryptic viremia not detectable in the blood. As shown in FIG. 6, $\hat{R}_{O_2}$ must be greater than 0.85, 0.86, 0.88 and 0.93 for diameter size of 2, 1.5, 1 and 0.5 mm respectively to have a detectable viral load in the most remote compartment. Above the critical threshold, the total viral load saturates quickly, and target-cell depletion determines the steady-state viral load. The conditions for cryptic viremia before intensification are related to the transient behavior of 2-LTR in blood after adding raltegravir. To better understand the role of $\hat{R}_{O_2}$ in the 2-LTR formation in blood after raltegravir intensification we plot the behavior of 2-LTR in compartment 1 after applying intensification for different diameters as shown in FIG. 5.

Note the smaller the size of the compartment, the higher the maximum value of 2-LTR in the main compartment after raltegravir intensification. This is because smaller compartments diffuse more rapidly into the blood. However, as shown in FIG. 6, the larger the site diameter the larger the value of $\hat{R}_{O_2}$ is required to allow viral replication. FIG. 5 also demonstrates that the smaller the site the greater $\hat{R}_{O_2}$ to find detectable 2-LTR peaks in the main compartment. More specifically $\hat{R}_{O_2}$ has to be in the range between 0.96-1 to find detectable 2-LTR peaks for diameter length from 0.5 to 2 mm. This implies that a significant reduction in drug efficacy throughout the site is necessary to explain the transient 2-LTR peaks observed in Reference 36. It is worth pointing out that the shape of the transient peaks predicted by the model, as shown in FIG. 5, match the median observed dynamics reported in Reference 36.

Figure 7:
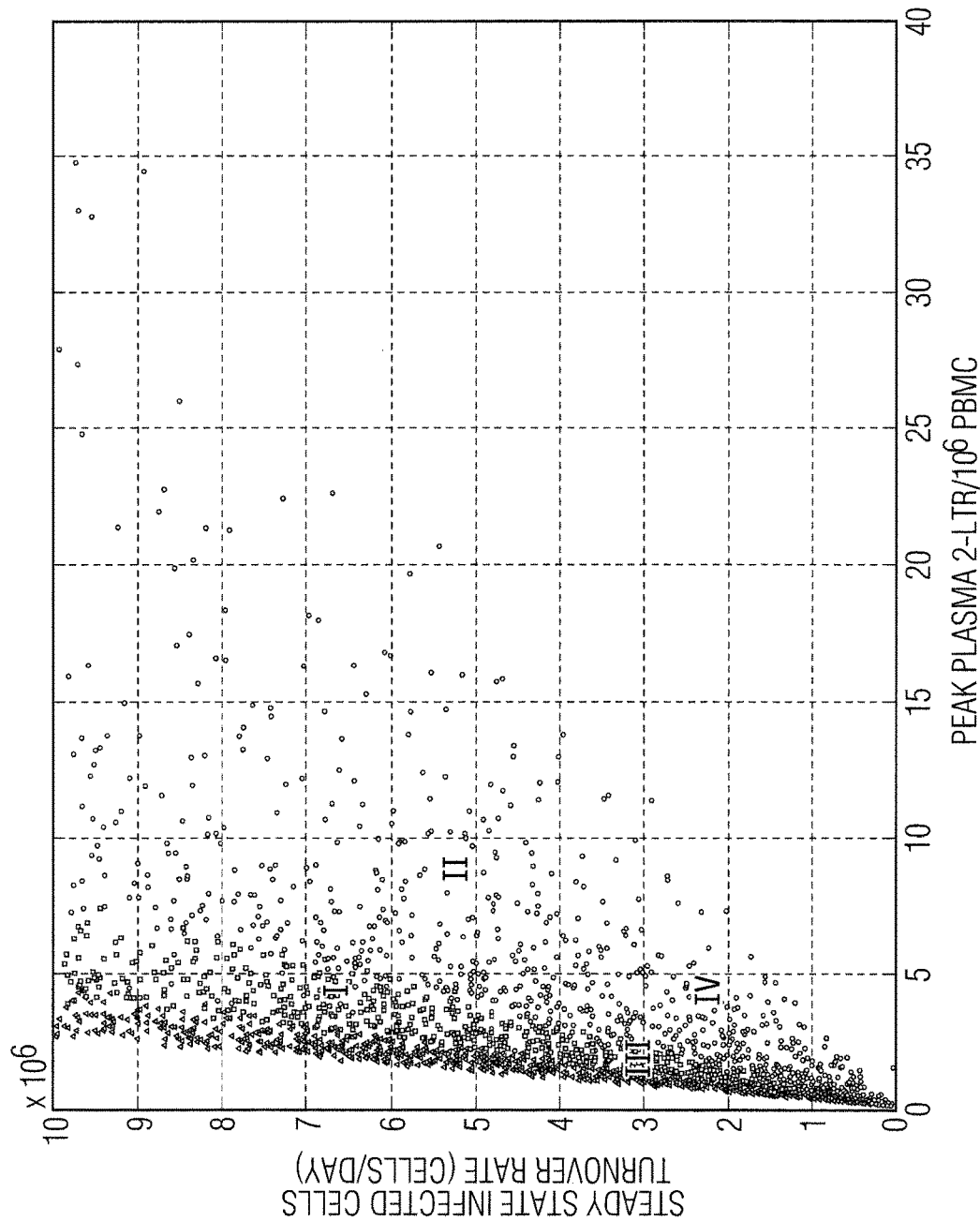
FIG. 7 shows regions of the scattered plot depending on the N compartments volume tissue and individual sphere diameter length. Region I, the largest tissue volume and diameter; region II, large tissue volume but small diameter; region III small tissue volume and large diameter; and region IV for small volume tissue and diameter.

To understand the relation between the total tissue volume, individual site size, infected T-Cell turnover rate and predicted 2-LTR peaks in compartment 1, a 10,000-trial Monte-Carlo simulation using the priors previously described with values of $\hat{R}_{O_2}$ drawn from the uniform distribution 0.93-1.5 and total tissue volume and individual sphere diameter drawn from the uniform distributions 30-499 mL and 0.1-2 mm respectively was run. The scatterplot in FIG. 7 shows the steady state value of the total infected cells turnover rate before intensification versus the maximum value of the 2-LTR transient behavior in blood.

There is a positive, approximately linear correlation between the 2-LTR peak and the T-Cell infection, suggesting that the 2-LTR peak post-intensification is a useful surrogate measurement of cryptic replication. In FIG. 7, the plot is divided into four regions according to the total tissue volume of all N sites and the diameter of each site. Region I has the largest tissue volume and diameter, region II, large tissue volume but small diameter, region III small tissue volume and large diameter and region IV for small volume tissue and diameter. In general, neither cryptic replication nor a 2-LTR peak is present when the site diameter is less than 0.4 mm. Larger peaks of 2-LTR positively correlate with greater total tissue volume as well as more infection, and weakly negatively correlate with site diameter, as long as the diameter is above the threshold necessary to allow replication. For total sanctuary site volumes above 30 mL, 2-LTR peaks in compartment 1 are larger than the limit of detection in greater than 95% of the cases.

Figure 8:
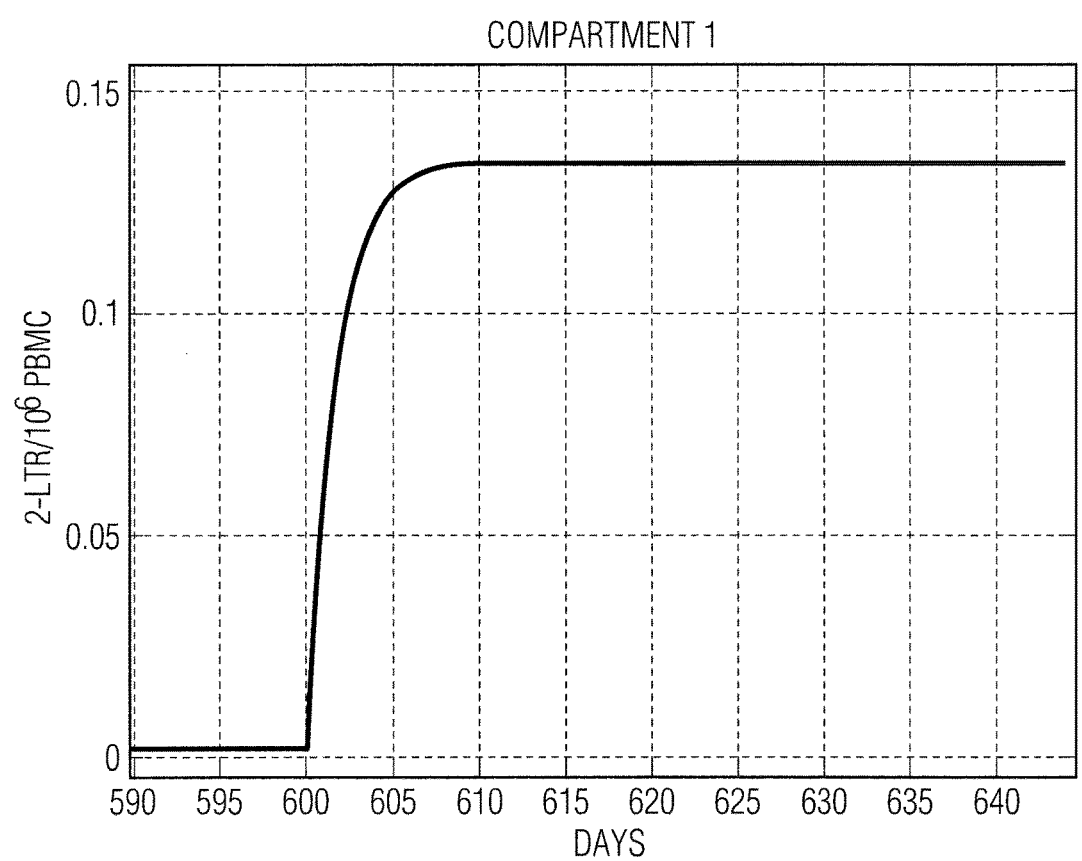
FIG. 8 shows monotonic 2-LTR dynamics in compartment 1 for all parameter values where $\hat{R}_{O_{10}} < 1$.

We also investigated the case where $\hat{R}_{O_{10}}$ is below 1; that is, only inefficient residual viremia is present in all compartments. Under these conditions, the predicted 2-LTR concentrations in compartment 1 following integrase inhibitor intensification always follow a monotonic, rather than a transient increase, as shown in FIG. 8. The maximum predicted value of 2-LTR in compartment 1 is below the limit of detections in normal assays (1.2 2-LTR/$10^6$ PBMC) for greater than 95% of the trials when $\hat{R}_{O_{10}}$ is below 1.

2.6 Calculating Pre-Intensification De Novo Infection Rate

From Equation 5, the turnover rate of actively infected cells prior to intensification (normalized to units of cells per $10^6$ peripheral-blood mononuclear cells per day) obeys the inequality given by Equation 17:

$$\alpha y(0) > \frac{k_H y_e}{1 - R} \tag{17}$$

This equation for ay(0) has units of infected cells per $10^6$ peripheral-blood mononuclear cells (PBMC) per day. In order to convert this into an estimate of the total number of de novo infected cells generated per day, we need an estimate of the number of PBMC per mL and an estimate of the effective total patient volume. There are between $1.1 \times 10^6$ and $3.7 \times 10^6$ PBMC/mL. A standard estimate for effective patient volume is 30 L (corresponding to a total patient volume of 100 L) as in Reference 62. These estimates give a minimum conversion factor of $$\left(\frac{1.1 \times 10^6 \, PBMC}{mL}\right) \times (30 \, L) = 3.3 \times 10^4 \frac{\text{infected cells} \times 10^6 PBMC}{2\text{-}LTR} \quad (18)$$

from measured peak 2-LTR concentration to minimum de novo infection rate prior to intensification.

2.7 Modeling Measurement Uncertainty

The measurement techniques used in this experiment are novel, and the number of replicates is insufficient to experimentally assign detection thresholds or standard deviations. We therefore estimate the measurement uncertainty from a probabilistic analysis of the measurement techniques and comparison to similar methods.

The technique first purifies an average of $6 \times 10^7$ PBMC, and uses 70% of these cells to quantify episomal DNA. This leads to an average of $4.2 \times 10^7$ PBMCs per sample, which means that one cell containing episomal DNA in the sample would correspond to a measurement of 0.024 2-LTR/$10^6$ PBMC. The purified sample is then amplified using a standard PCR assay. When this assay is used to amplify HIV-1 RNA, it has a very conservative published limit of quantification of 50 virions per mL from a 1 mL sample. Using this same 50 copy sensitivity limit, we arrive at an equivalent limit of detection for the 2-LTR assay of 1.2 2-LTR/$10^6$ PBMC. The reported data from Reference 36 included four non-zero measurements below this limit—we treated these measured values as censored for our analysis. The PCR process introduces log-normal uncertainty in the 2-LTR estimates, which has been shown to increase as the expected copy number decreases. We interpolated between the measured standard deviations for viral loads from 50 copies per mL and $10^4$ copies per mL as reported in Reference 64 using the theoretical relationship between expected copy number and log-normal standard deviation derived in Reference 65, arriving at a the formula for density-dependent log-normal standard deviation in $\log_{10}$ units:

$$\sigma(c) = 10^{-0.21 - 0.24 \, \log_{10}(42 \times c)} \quad (19)$$

As shown in Reference 66, this interpolation function fits all measured data points from Reference 64 to within two significant digits. This gives a log-normal standard deviation that ranges from 0.24 $\log_{10}$ at the limit of detection of 1.2 2-LTR/$10^6$ PBMC to 0.09 $\log_{10}$ for the highest measured valued of 72 2-LTR/$10^6$ PBMC. The values of u are truncated outside of the range 0.08-0.24 $\log_{10}$.

Given the model for limit of quantification and log-normal standard deviation described above, we arrive at a likelihood function for a measured 2-LTR concentration m given a modeled 2-LTR concentration c:

$$L(c|m) = \begin{cases} f_{LN}(m, c, \sigma(c)) & , m > 1.2 \\ F_{LN}(1, 2, c, \sigma(1.2)) & , m = 1.2 \end{cases} \quad (20)$$

where $f_{LN}$ is the log-normal PDF and $F_{LN}$ is the log-normal CDF. This follows the standard Tobit model for censored measurements.

2.8 Identifiability Analysis

With prior knowledge of a, the parameter set $\{R; \eta_{II}; \varphi; \delta; k_{II}y_e\}$ is identifiable from c. The current best estimate for the value of a based on in vivo experiments is $1 \pm 0.3$ day$^{-1}$; we use a nominal value of $a=1$ day$^{-1}$. It is shown in the supplemental material that the estimates of the other parameters are insensitive to variation of a within the range described.

2.9 Model Fit

We identified the parameters of Equation 5 subject to the experimental data using a nonlinear mixed effects model. Nonlinear mixed-effects models are useful for identifying parameter values for repeated experiments when there is a reasonable expectation that certain parameters have consistent values between trials; they also allow us to borrow information across subjects to compensate when sparse data is available for individual subjects. These formulations have been used many times previously for HIV model parameter estimation.

To reduce the parametric covariance, we introduced a re-parametrized parameter $A = k_{II}y_e/\delta$ to replace $k_{II}y_e$. While all five parameters are identifiable in theory, the sparsity of the measurements required considering two parameters to be fixed effects, with a common value for all patients. There is no reason to assume that either the decay rate of 2-LTR containing cells or the ratio of 2-LTR production in the presence vs. absence of raltegravir would vary significantly between patients, so the parameters $\{\varphi, \delta\}$ were considered fixed effects, with no inter-patient variation, and the parameters $\{R, \eta_{II}, A\}$ were considered random effects, subject to inter-patient variation, yielding the nonlinear mixed-effects problem formulation:

$$m_i(t_{i,k}) = \max\{c(t_{i,k}, \varphi, A_i, \eta_{IIi}, R_i) + e_{i,k}, 1.2\}$$

$$e_{i,k} \sim LN(0, \sigma^2(c)) \quad (21)$$

where $m_i(t_{i,k})$ is the i-th patient's measured 2-LTR count at time $t_{i,k}$, $e_{i,k}$ is log-normally distributed zero-mean measurement variance, c(•) is Equation 2 evaluated for the parameter set for the given patient, and $\sigma(c)$ is given by Equation 19.

The posterior distribution of the parameter likelihood given the measured 2-LTR values was computed using a Bayesian Markov-Chain Monte-Carlo method with Gibbs Sampling, as in References 56, 75, 78 and 79 with noninformative prior distributions for the parameters as follows:

$$\begin{cases} \delta \sim LN(0.6, 0.5) \\ \phi \sim LN(0.001, 1) \\ R \sim U(0, 1) \\ \eta_{II} \sim U(0, 1) \\ A \sim LN(\mu_i, 2.5) \end{cases} \quad (22)$$

where LN is the log-normal distribution, U is the uniform distribution, and $\mu_i$ is a patient specific mean arrived at through simulated-annealing based optimization. The histograms of the posterior distribution were analyzed to obtain the median, mode, and confidence interval estimates reported in Table 3.

Identifiability Analysis Details

A scaling substitution $$y = \frac{w}{k_{II}}$$

into Equation 1 yields the form:

$$\dot{w} = -a(1 - R + (R - R(1 - \eta_{II}))u_{II})w + k_{II}y_e$$

$$\dot{c} = a(\varphi R + (1 - \varphi)(R - R(1 - \eta_{II}))u_{II})w - \delta c \quad (23)$$

Assuming that c is the only measurable quantity, we find that the observability matrix for this system is non-singular, guaranteeing both observability of the states and identifiability of the parameters $\{a(1-R), a(1-R(1-\eta_{II})), k_{II}y_e; a\varphi R; a(R-(1-\theta)R(1-\eta_{II})), \delta\}$, assuming sufficiently many measurements under the conditions $\{u_{II}=0; u_{II}=1\}$. Assuming prior knowledge of the parameter a allows us to simplify this set of identifiable parameters to $\{R; \eta_{II}, \varphi, \delta, k_{II}y_e\}$.

Additional Details on the Bayesian MCMC Methods and Results

Figure 9:
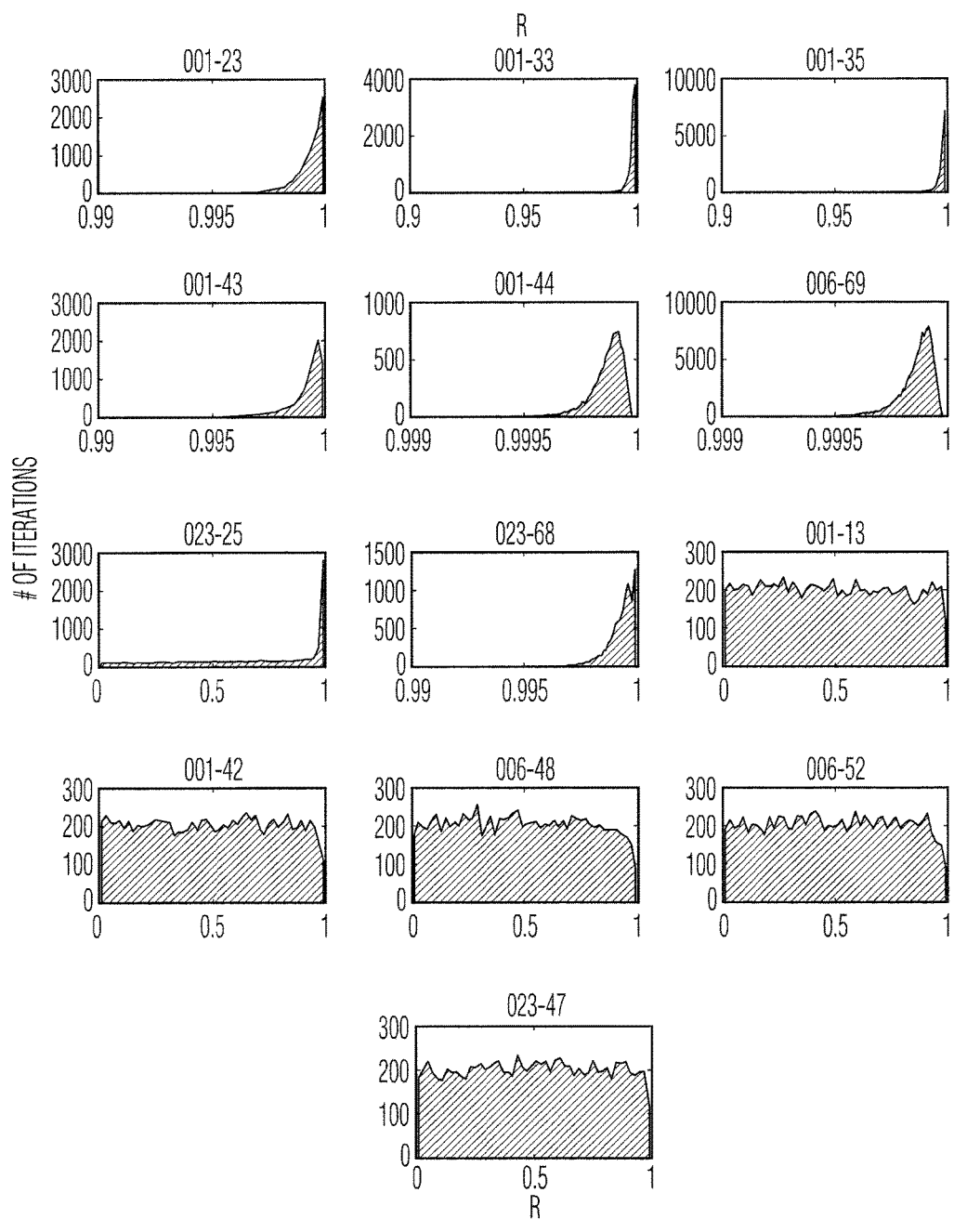
FIG. 9 shows the posterior distribution of the parameter R for 13 patients.

FIG. 9 shows the posterior distribution of the parameter R for 13 patients. R is bounded by definition between 0 and 1, so the prior uniform distribution between 0 and 1 is non-informative. The posterior distributions for patients 001-13, 001-42, 006-48, 006-52, and 023-47 are not noticeably different from the prior distributions, implying very little information about R in the measured data from these patients.

Figure 10:
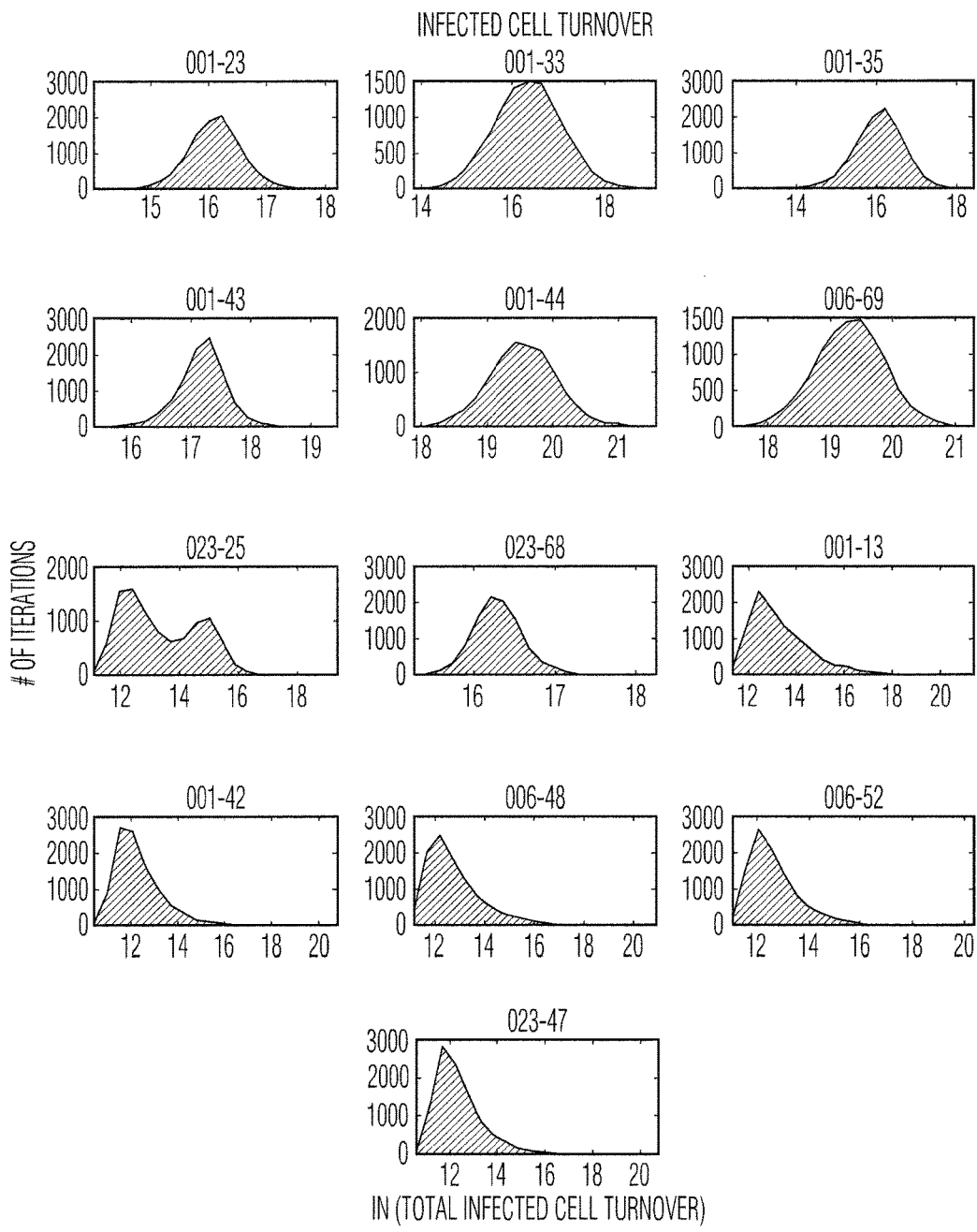
FIG. 10 shows infected cell turnover rate posterior distribution of the logarithm of the whole-body estimated infected cell turnover rate for 13 patients.

FIG. 10 shows the posterior distribution of the estimated whole-body infected cell turnover rates prior to raltegravir intensification for 13 patients. This parameter was not directly identified; instead it was derived from the identified values of the other five parameters.

A Note on Insensitivity to the Value of a

The parameter a enters Equation 1 as a coefficient of $(1-R)$ when $u_{II}=0$ and as a coefficient of $(1-(1-\eta_{II})R)$ when $u_{II}=1$. A change in the prior value of a from $a^{old}$ to $a^{new}$ will result in an identical fit to the data if R and $(1-\eta_{II})R$ are modified according to the equations:

$$R^{new} = 1 - \frac{a^{old}(1-R_{old})}{a^{new}} \text{ and } (1-\eta_{II})R^{new} = 1 - \frac{a^{old}(1-(I-\eta_{II}R^{old}))}{a^{new}}.$$

Note that for values of R close to 1, a 30% change in the assumed value of a would result in a 30% change in the value of 1−R, or a negligible change in the value of R.

3. Results 3.1 Experimental Results

The experimental results have been previously published in References 36 and 37. The measured 2-LTR concentrations from the 13 patients in the experimental group with non-zero 2-LTR measurements are shown in Table 2, corrected for a limit of quantification of 1.2 2-LTR per $10^6$ Peripheral-Blood Mononuclear Cells. The plasma viral load remained below the standard limit of detection for the duration of the experiment.

3.2 Model Fit

Figure 3:
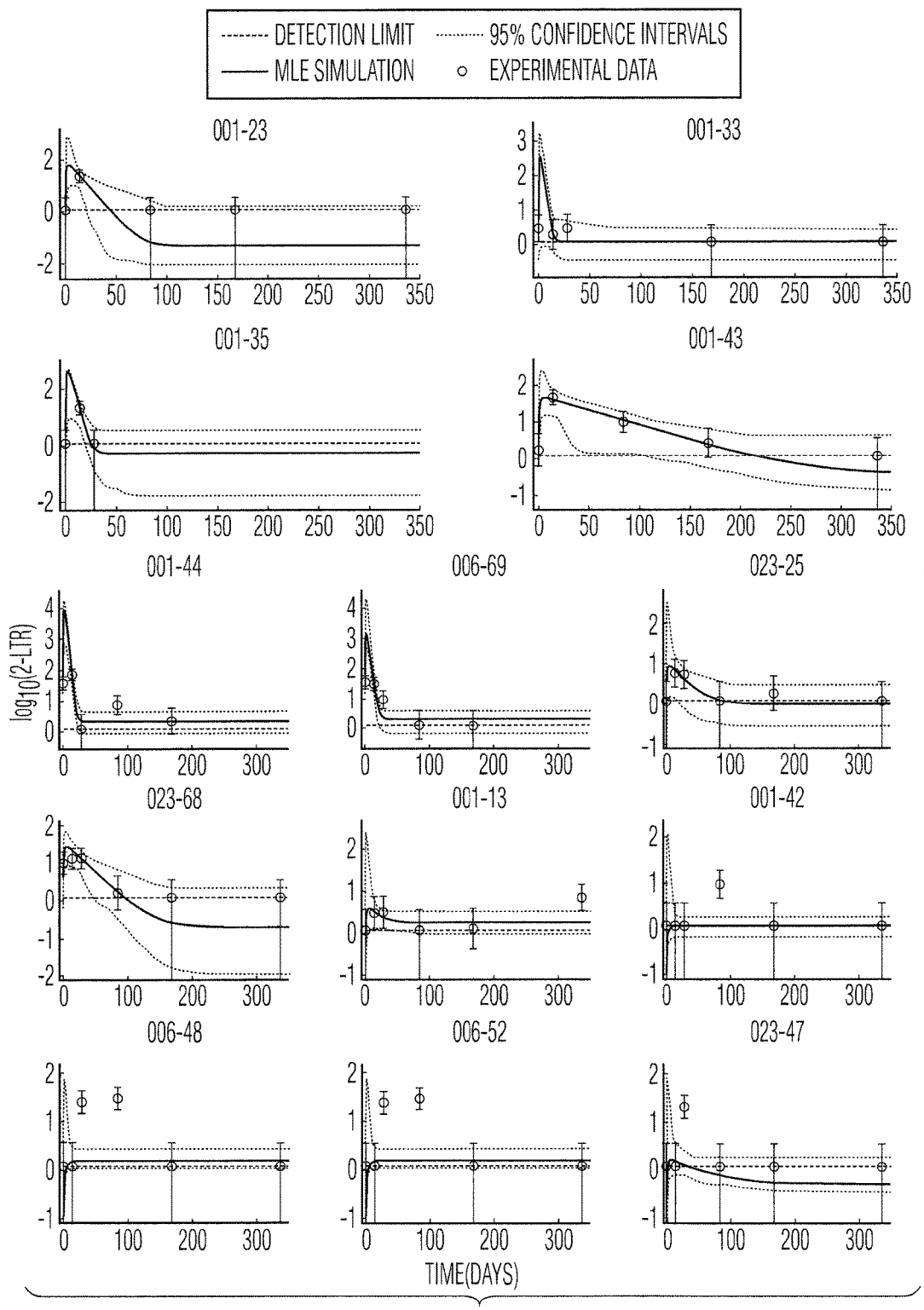
FIG. 3 shows maximum likelihood prediction and 95% Credible prediction intervals compared to measured data for 13 patients.

Markov-Chain Monte-Carlo methods were used to fit Equation 5 to the experimental data for 13 patients, with shared parameters $\{\theta, \delta\}$ and patient-specific parameters $\{R; \eta_{II}, k_{II}y_e\}$, using the measurement uncertainty model described in the Materials and Methods section. Hypothesis $H_1$ had a statistically significant fit to the data, with $P<10^{-5}$ from the log-likelihood ratio test and a $\Delta AICc$ of −143 compared to the null hypothesis $H_0$ of random variation about the mean value, giving the null hypothesis $H_0$ a residual likelihood of less than $10^{-5}$. The maximum-likelihood predicted 2-LTR concentrations for each patient, together with the 95% prediction interval, is shown compared to the measured data in FIG. 3.

The Maximum Likelihood (Posterior Mode), Median, and 95% Credible Interval values for the parameters for each patient are shown in Table 3.

3.3 Parameter Estimates

The estimated decay rate $\delta$ of the measured 2-LTR had a median estimate of 0.47 and a 95% Credible Interval of 0.36-0.83×day$^{-1}$, slightly faster than the previously estimated in vivo rates of $$\frac{0.04}{\text{day}} - \frac{0.4}{\text{day}}.$$

The ratio $\varphi$ between the likelihood of 2-LTR formation during an infection event uninterrupted by raltegravir to the likelihood of 2-LTR formation if raltegravir interrupted the infection event had a median estimate of 0.002 and a 95% credible interval of 0.001-0.004; interruption of integration by raltegravir makes 2-LTR formation approximately 250-1000 times more likely. These estimates are consistent with the increased production of 2-LTR in the presence of raltegravir both in vitro and in vivo.

For seven patients (Patients 001-23, 001-33, 001-35, 001-43, 001-44, 006-69, and 023-68), the median, maximum-likelihood, and 95% Credible Intervals for the pre-intensification reproductive ratio R are lower-bounded by 0.99, implying the presence of uncontrolled, cryptic replication of the virus in these patients prior to raltegravir intensification. For Patient 023-25, the maximum-likelihood estimate of R=0.9940 is consistent with cryptic replication, but the data does not sufficiently constrain this estimate, resulting in a long-tailed posterior distribution and broad confidence intervals. For the remaining five patients, the posterior distribution of R is not significantly different from the prior uniform distribution between 0 and 1, demonstrating that there was very little information about this parameter in the measured data for these patients.

The scaled rate of exogenous infected cell entry $k_{II}y_e$ was remarkably consistent, with median estimates bounded between 0.2 and 2.1 2-LTR circles×$(10^6 \text{ PBMC})^{-1}$×day$^{-1}$ for all 13 patients. The probability $k_{II}$ is upper-bounded by 1, so these rates provide an lower bound on the median estimate of $y_e$ of 0.2 infected cells per million peripheral blood mononuclear cells per day, a rate consistent with quiescent cell activation. Since $k_{II}$ is not uniquely identifiable from the data, an upper bound cannot be obtained.

The residual efficacy of raltegravir $\eta_{II}$ was poorly constrained by the data, with tight credible intervals available only for 5 of the thirteen patients. The sampling rate in this experiment is too low to obtain tight bounds on this parameter for most patients in the study.

4. Discussion

We have introduced a new model to account for the formation of 2-LTR circles in the presence and absence of raltegravir intensification, and validated this model against patient data from a raltegravir intensification study. The data was shown to overwhelmingly favor our model when compared to the null hypothesis. Tightly bounded estimates were obtained for the shared parameters $\varphi$ and $\delta$. Tightly bounded estimates for the patient-specific parameters R, $\eta_{II}$, and $k_{II}y_e$ were obtained for a subset of the patients, with broader confidence intervals obtained for the other patients. Since all parameters are theoretically identifiable from the data, the broad confidence intervals for these patients do not in any way reduce the confidence in the tight intervals found for the other patients. The primary reason for the broad confidence intervals appears to be a relatively low sampling rate. If the experiment were repeated with higher-frequency measurements, tighter confidence intervals on all five parameters could be obtained. Conversely, experiments that sample 2-LTR concentrations less frequently following intensification (i.e., 12 week intervals, and 4 week intervals) are likely to miss the observed peaks altogether.

Tight bounds on the infection success ratio R were obtained for 7 of the 13 patients, showing that good fits to the data for these patients were only consistent with R in the range 0.99<R<1. As discussed previously, a finding that the measured reproductive ratio is essentially equal to 1 is consistent with the hypothesis that ongoing efficient replication is occurring in a sanctuary site with poor antiviral drug penetration. Many candidates for potential sanctuary sites have previously been identified. For these seven patients, the measured data are also inconsistent with the alternative hypothesis that the measured 2-LTR were formed through limited rounds of infection primarily sourced from the activation of quiescently infected cells. If this were the case, then measured R would range between 0.1-0.8 and the increase in measured 2-LTR would be followed by little or no decrease, as shown in FIG. 2. This alternative hypothesis is not ruled out for the other six patients in the study.

The observed dynamics of 2-LTR circles in the blood allow us to calculate minimum turnover rates for the efficient replication occurring in these patients. As seen in Table 4, the median estimates for pre-intensification infected cell turnover in the seven patients exhibiting efficient replication range from between 10 million infected cells per day up to 310 million infected cells per day. If the virus produced by this level of ongoing infection diffused freely through the patient, this would correspond to measured plasma viremia well above the standard limit of detection; this is not observed, consistent with the cryptic replication hypothesis, with replication occurring in a sanctuary site. To explain the data, the sanctuary site would have to reside in an anatomical location where the average diffusion time to the blood of a free virus was longer than its 30 minute half-life, the average diffusion time to the blood of an infected cell was longer than its 0.7 day half-life, but the average diffusion time to the blood of a 2-LTR containing cell was shorter than its approximately 1.5 day half-life.

4.1 Clinical Significance

The level of efficient replication indicated by the patterns of measured 2-LTR in circulating PBMC following treatment intensification by raltegravir is quite high. Replication rates of $1 \times 10^7$ cells×day$^{-1}$ are high enough to make it likely that important resistance mutations are generated, and the fact that the replication is occurring in a site that allows for efficient replication makes it possible for the mutated cells to persist long enough to acquire additional mutations. This would provide a mechanism for sequentially acquiring the multi-drug resistance necessary to escape therapy, and would explain the experimental results showing evidence of such a lineage of acquired mutations in episomal DNA recovered from patients who experience treatment failure.

It is also interesting that this level of replication is occurring in patients who have measured plasma viral loads persistently below the detection threshold. This implies that this replication is cryptic, unobservable from standard viral load assays. The existence of cryptic, efficient replication of HIV in patients with plasma viremia persistently below the limit of detection is a troubling result.

The data seem to indicate that the addition of raltegravir reduces the level of cryptic replication to undetectable levels. There are a number of possible explanations for this. The addition of raltegravir could cause the residual activity of the antiviral drugs to cross a threshold of efficacy, bringing the basic reproductive ratio of the virus in the site of 2-LTR formation below 1. In this case, the effect is not unique to raltegravir, but is instead merely a result of using four antiviral drugs simultaneously. It is also possible that the properties of raltegravir allow it to penetrate the site of 2-LTR formation better than the other antiviral drugs. The experiment does not provide sufficient data to distinguish between these hypotheses.

It is important to remember that of the 45 patients in the experimental group, only 13 had any nonzero measurements of 2-LTR containing cells. This proportion is consistent with previous studies showing the existence of non-overlapping 2-LTR positive and 2-LTR negative patient subgroups. Of these 13, only 7 had dynamics consistent with efficient cryptic viremia. This is consistent with efficient cryptic viremia rates in the treated HIV patient population of between 6% and 29%. Therefore, these findings may only apply to a small subset of patients; further study will be necessary to determine whether cryptic viremia is more widespread.

Finally, the limited data available in this experiment forced us to use a reduced model of 2-LTR dynamics following raltegravir intensification. While this reduced model exhibited excellent fit to the measured data, it neglects many sources of more complicated dynamics in the system, including the dynamics of target cell recovery and the spatial dynamics of diffusion from the sanctuary site to the blood. While we believe that the model simplifications employed in this study are valid, it is clear that a follow-up experiment, with a significantly higher frequency of measurement of 2-LTR concentrations, will be necessary to further validate the model and explore the higher-order dynamics introduced by the phenomenon neglected in this study. This will allow us to determine whether efficient cryptic replication remains the best explanation of the observed transient peaks in measured 2-LTR following raltegravir intensification, or whether more complicated models can provide a better explanation.

Various terms relating to the systems, methods, and other aspects of the present invention are used throughout the specification and claims. Such terms are to be given their ordinary meaning in the art unless otherwise indicated.

All documents, books, manuals, papers, patents, published patent applications, guides, abstracts, and/or other references cited herein are incorporated by reference in their entireties. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

REFERENCES

1. Hatano H, Vogel S, Yoder C, Metcalf J A, Dewar R, Davey R T, et al. Pre-HAART HIV burden approximates post-HAART viral levels following interruption of therapy in patients with sustained viral suppression. AIDS. 2000 July; 14(10): 1357-1363.

2. Chun T W, Davey R T, Ostrowski M, Shawn Justement J, Engel D, Mullins J I, et al. Relationship between pre-existing viral reservoirs and the re-emergence of plasma viremia after discontinuation of highly active anti-retroviral therapy. Nat Med. 2000 July; 6(7):757-761.
3. Chun T W, Davey R T, Engel D, Lane H C, Fauci A S. Re-emergence of HIV after stopping therapy. Nature. 1999 October; 401(6756):874-875.
4. Davey R, Bhat N, Yoder C, Chun T, Metcalf J, Dewar R, et al. HIV-1 and T cell dynamics after interruption of highly active antiretroviral therapy (HAART) in patients with a history of sustained viral suppression. Proc Natl Acad Sci USA. 1999 December; 96(26):15109-15114.
5. Wong J K, Hezareh M, GOnthard H F, Havlir D V, Ignacio C C, Spina C A, et al. Recovery of replication-competent HIV despite prolonged suppression of plasma viremia. Science. 1997 November; 278(5341):1291-1295.
6. Palmer S, Wiegand A P, Maldarelli F, Bazmi H, Mican J M, Polis M, et al. New real-time reverse transcriptase-initiated PCR assay with single-copy sensitivity for human immunodeficiency virus type 1 RNA in plasma. 3 Clin Microbiol. 2003 October; 41(10):4531-4536.
7. Trono D, Van Lint C, Rouzioux C, Verdin E, Barre-Sinoussi F, Chun T W, et al. HIV persistence and the prospect of long-term drug-free remissions for HIV-infected individuals. Science. 2010 July; 329(5988): 174-180.
8. Hatano H, Delwart E L, Norris P J, Lee T H, Neilands T B, Kelley C F, et al. Evidence of persistent low-level viremia in long-term HAART-suppressed, HIV-infected individuals. AIDS. 2010 October; 24(16):2535-2539.
9. Nettles R E, Kieer T L, Kwon P, Monie D, Han Y, Parsons T, et al. Intermittent HIV-1 viremia (Blips) and drug resistance in patients receiving HAART. JAMA. 2005 February; 293(7):817-829.
10. Persaud D, Siberry G K, Ahonkhai A, Kajdas 3, Monie D, Hutton N, et al. Continued production of drug-sensitive human immunodeficiency virus type 1 in children on combination antiretroviral therapy who have undetectable viral loads. J Virol. 2004 jan; 78(2):968-979.
11. Maldarelli F, Palmer S, King M S, Wiegand A, Polis M A, Mican 3, et al. ART suppresses plasma HIV-1 RNA to a stable set point predicted by pretherapy viremia. PLoS Pathog. 2007 April; 3(4):e46.
12. Dornadula G, Zhang H, VanUitert B, Stern J, Livornese L, Ingerman M J, et al. Residual HIV-1 RNA in blood plasma of patients taking suppressive highly active antiretroviral therapy. JAMA. 1999 November; 282(17): 1627-1632.
13. Josefsson L, Dahl V, Palmer S. Can HIV infection be eradicated through use of potent antiviral agents?Curr Opin Infect Dis. 2010 December; 23(6):628-632.
14. Maldarelli F. Targeting viral reservoirs: ability of antiretroviral therapy to stop viral replication. Curr Opin HIV AIDS. 2011 jan; 6(1):49-56.
15. Siliciano J D, Siliciano R F. Biomarkers of HIV replication. Curr Opin HIV AIDS. 2010 November; 5(6):491-497.
16. Tobin N H, Learn G H, Holte S E, Wang Y, Melvin A J, McKernan J L, et al. Evidence that low-level viremias during effective highly active antiretroviral therapy result from two processes: expression of archival virus and replication of virus. J Virol. 2005 August; 79(15):9625-9634.
17. Sharkey M, Babic D Z, Greenough T, Gulick R, Kuritzkes D R, Stevenson M. Episomal viral cDNAs identify a reservoir that fuels viral rebound after treatment interruption and that contributes to treatment failure. PLoS Pathog. 2011 February; 7(2):e1001303.
18. Cohen J. HIV/AIDS research. Tissue says blood is misleading, confusing HIV cure efforts. Science. 2011 December; 334(6063):1614.
19. Lambotte O, Chaix M L, Gubler B, Nasreddine N, Wallon C, Goujard C, et al. The lymphocyte HIV reservoir in patients on long-term HAART is a memory of virus evolution. AIDS. 2004 May; 18(8):1147-1158.
20. Cintron-Arias A, Castillo-Chavez C, Bettencourt L M A, Lloyd A L, Banks H T. The estimation of the effective reproductive number from disease outbreak data. Math Biosci Eng. 2009 April; 6(2):261-282.
21. Anderson J A, Archin N M, Ince W, Parker D, Wiegand A, Coffin J3M, et al. Clonal sequences recovered from plasma from patients with residual HIV-1 viremia and on intensified antiretroviral therapy are identical to replicating viral RNAs recovered from circulating resting CD4+ T cells. J Virol. 2011 May; 85(10):5220-5223.
22. Kieffer T L, Finucane M M, Nettles R E, Quinn T C, Broman K W, Ray S C, et al. Genotypic analysis of HIV-1 drug resistance at the limit of detection: virus production without evolution in treated adults with undetectable HIV loads. J Infect Dis. 2004 April; 189(8):1452-1465.
23. Hermankova M, Ray S C, Ruff C, Powell-Davis M, Ingersoll R, D'Aquila R T, et al. HIV-1 drug resistance profiles in children and adults with viral load of <50 copies/mL receiving combination therapy. JAMA. 2001 July; 286(2):196-207.
24. Bailey J R, Sedaghat A R, Kieffer T, Brennan T, Lee P K, Wind-Rotolo M, et al. Residual human immunodeficiency virus type 1 viremia in some patients on antiretroviral therapy is dominated by a small number of invariant clones rarely found in circulating CD4+ T cells. J Virol. 2006 July; 80(13):6441-6457.
25. Evering T H, Mehandru S, Racz P, Tenner-Racz K, Poles M A, Figueroa A, et al. Absence of HIV-1 evolution in the gut-associated lymphoid tissue from patients on combination antiviral therapy initiated during primary infection. PLoS Pathog. 2012 February; 8(2):e1002506.
26. Dinoso J B, Kim S Y, Wiegand A M, Palmer S E, Gange S J, Cranmer L, et al. Treatment intensification does not reduce residual HIV-1 viremia in patients on highly active antiretroviral therapy. Proc Natl Acad Sci USA. 2009 June; 106(23):9403-9408.
27. McMahon D, Jones J, Wiegand A, Gange S J, Kearney M, Palmer S, et al. Short-Course Raltegravir Intensification Does Not Reduce Persistent Low-Level Viremia in Patients with HIV-1 Suppression during Receipt of Combination Antiretroviral Therapy. Clinical Infectious Diseases. 2010 March; 50(6):912-919.
28. Gandhi R T, Coombs R W, Chan E S, Bosch R J, Zheng L, Margolis D M, et al. No effect of raltegravir intensification on viral replication markers in the blood of HIV-1-infected patients receiving antiretroviral therapy. J Acquir Immune Defic Syndr. 2012 March; 59(3):229-235.
29. Pauza C D, Trivedi P, McKechnie T S, Richman D D, Graziano F M. 2-LTR circular viral DNA as a marker for human immunodeficiency virus type 1 infection in vivo. Virology. 1994 December; 205(2):470-478.

30. Sharkey M E, Teo I, Greenough T, Sharova N, Luzuriaga K, Sullivan J L, et al. Persistence of episomal HIV-1 infection intermediates in patients on highly active antiretroviral therapy. Nat Med. 2000 January; 6(1):76-81.
31. Morlese J, Teo I A, Choi J W, Gazzard B, Shaunak S. Identification of two mutually exclusive groups after long-term monitoring of HIV DNA 2-LTR circle copy number in patients on HAART. AIDS. 2003 March; 17(5):679-683.
32. Pierson T C, Kieffer T L, Ruff C T, Buck C, Gange S J, Siliciano R F. Intrinsic stability of episomal circles formed during human immunodeficiency virus type 1 replication. J Virol. 2002 April; 76(8):4138-4144.
33. Butler S L, Johnson E P, Bushman F D. Human immunodeficiency virus cDNA metabolism: notable stability of two-long terminal repeat circles. J Virol. 2002 April; 76(8):3739-3747.
34. Bushman F. Measuring covert HIV replication during HAART: the abundance of 2-LTR circles is not a reliable marker. AIDS. 2003 March; 17(5):749-750.
35. Zhu W, Jiao Y, Lei R, Hua W, Wang R, Ji Y, et al. Rapid turnover of 2-LTR HIV-1 DNA during early stage of highly active antiretroviral therapy. PLoS ONE. 2011; 6(6):e21081.
36. Buzòn M J, Massanella M, Llibre J M, Esteve A, Dahl V, Puertas M C, et al. HIV-1 replication and immune dynamics are affected by raltegravir intensification of HAART-suppressed subjects. Nat Med. 2010 April; 16(4):460-465.
37. Llibre J M, Buzòn M J, Massanella M, Esteve A, Dahl V, Puertas M C, et al. Treatment intensification with raltegravir in subjects with sustained HIV-1 viremia suppression: a randomized 48 weeks study. Antivir Ther (Lond). 2012 June; 17:355-364.
38. Murray J M. HIV dynamics and integrase inhibitors. Antivir Chem Chemother. 2009; 19(4):157-164.
39. Murray J M, Emery S, Kelleher A D, Law M, Chen J, Hazuda D J, et al. Antiretroviral therapy with the integrase inhibitor raltegravir alters decay kinetics of HIV, significantly reducing the second phase. AIDS. 2007 November; 21(17):2315-2321.
40. Friedrich B, Li G, Dziuba N, Ferguson M R. Quantitative PCR used to assess HIV-1 integration and 2-LTR circle formation in human macrophages, peripheral blood lymphocytes and a CD4+ cell line. Virol J. 2010; 7:354.
41. Reigadas S, Andreola M L, Wittkop L, Cosnefroy O, Anies G, Recordon-Pinson P, et al. Evolution of 2-long terminal repeat (2-LTR) episomal HIV-1 DNA in raltegravir-treated patients and in in vitro infected cells. J Antimicrob Chemother. 2010 March; 65(3):434-437.
42. Perelson A. Dynamics of HIV infection of CD4+ T cells. Mathematical Biosciences. 1993 March; 114(1):81-125.
43. Sedaghat A R, Siliciano R F, Wilke C O. Constraints on the dominant mechanism for HIV viral dynamics in patients on raltegravir. Antivir Ther (Lond). 2009; 14(2):263-271.
44. Cardozo E F, Vargas C A, Zurakowski R. A Compartment Based Model for the Formation of 2-LTR Circles after Raltegravir Intensification. In: 51st IEEE Conference on Decision and Control. Maui, Hi.; 2012. p. 4924-4929.
45. von Andrian U H, Mempel T R. Homing and cellular traffic in lymph nodes. Nat Rev Immunol. 2003 November; 3(11):867-878.
46. Mirsky H P, Miller M J, Linderman J J, Kirschner D E. Systems biology approaches for understanding cellular mechanisms of immunity in lymph nodes during infection. 3 Theor Biol. 2011 October; 287:160-170.
47. Girard J P, Moussion C, Förster R. HEVs, lymphatics and homeostatic immune cell trafficking in lymph nodes. Nat Rev Immunol. 2012 November; 12(11):762-773.
48. Beltman J B, Maree A F M, Lynch J N, Miller M J, De Boer R J. Lymph node topology dictates T cell migration behavior. J Exp Med. 2007 April; 204(4):771-780.
49. Kirschner D, Webb G F, Cloyd M. Model of HIV-1 disease progression based on virus-induced lymph node homing and homing-induced apoptosis of CD4+ lymphocytes. J Acquir Immune Defic Syndr. 2000 August; 24(4):352-362.
50. Baldazzi V, Paci P, Bernaschi M, Castiglione F. Modeling lymphocyte homing and encounters in lymph nodes. BMC Bioinformatics. 2009; 10:387.
51. Marinho E B S, Bacelar F S, Andrade R F S. A model of partial differential equations for HIV propagation in lymph nodes. Physica A: Statistical Mechanics and its Applications. 2012 January; 391(1-2): 132-141.
52. Callaway D S, Perelson A S. HIV-1 infection and low steady state viral loads. Bull Math Biol. 2002 January; 64(1):29-64.
53. Rong L, Perelson A S. Modeling latently infected cell activation: viral and latent reservoir persistence, and viral blips in HIV-infected patients on potent therapy. PLoS Comput Biol. 2009 October; 5(10):e1000533.
54. Nowak M, May R. Virus Dynamics: Mathematical Principles of Immunology and Virology. New York; 2000.
55. Luo R, Cardozo E F, Piovoso M J, Wu H, Buzon M J, Martinez-Picado J, et al. Modeling 2-LTR Formation Following Raltegravir Intensification. Journal of the Royal Society Interface; p. (submitted).
56. Luo R, Piovoso M J, Martinez-Picado J, Zurakowski R. HIV model parameter estimates from interruption trial data including drug efficacy and reservoir dynamics. PLoS ONE. 2012 July; 7(7):e40198.
57. Crosley L K, Duthie S J, Polley A C, Bouwman F G, Helm C, Mulholland F, et al. Variation in protein levels obtained from human blood cells and biofluids for platelet, peripheral blood mononuclear cell, plasma, urine and saliva proteomics. Genes Nutr. 2009 jun; 4(2):95-102.
58. Orenstein J M, Feinberg M, Yoder C, Schrager L, Mican J M, Schwartzentruber D J, et al. Lymph node architecture preceding and following 6 months of potent antiviral therapy: follicular hyperplasia persists in parallel with p24 antigen restoration after involution and CD4 cell depletion in an AIDS patient. AIDS. 1999 November; 13(16):2219-2229.
59. Swartz M A. The physiology of the lymphatic system. Adv Drug Deliv Rev. 2001 August; 50(1-2):3-20.
60. Lai B E, Henderson M H, Peters J J, Walmer D K, Katz D F. Transport theory for HIV diffusion through in vivo distributions of topical microbicide gels. Biophys J. 2009 November; 97(9):2379-2387.
61. Murray A G, Jackson G A. Viral dynamics: a model of the effects of size, shape, motion and abundance of single-celled planktonic organisms and other particles. Mar Ecol Prog Ser. 1992 November; 89:103-116.
62. Colgrove R, Japour A. A combinatorial ledge: reverse transcriptase fidelity, total body viral burden, and the implications of multiple-drug HIV therapy for the evolution of antiviral resistance. Antiviral Res. 1999 February; 41(1):45-56.
63. Armbruster D A, Pry T. Limit of blank, limit of detection and limit of quantitation. Clin Biochem Rev. 2008 August; 29 Suppl 1:S49-52.

64. Perrin L, Pawlotsky J M, Bouvier-Alias M, Sarrazin C, Zeuzem S, Colucci G. Multicenter performance evaluation of a new TaqMan PCR assay for monitoring human immunodeficiency virus RNA load. J Clin Microbiol. 2006 December; 44(12):4371-4375.
65. Bengtsson M, Hemberg M, Rorsman P, Stahlberg A. Quantification of mRNA in single cells and modelling of RT-qPCR induced noise. BMC Mol Biol. 2008; 9:63.
66. Luo R, Piovoso M J, Zurakowski R. Modeling Uncertainty in Single-Copy Assays for HIV. J Clin Microbiol. 2012 July; 50(10):3382-3383.
67. Tobin J. Estimation of Relationships for Limited Dependent Variables. Econometrica. 1958 January; 26(1):24-36.
68. Tse E, Anton J J. On the identifiability of parameters. IEEE Transactions on Automatic Control. 1972; 17(5): 637-646.
69. Markowitz M, Louie M, Hurley A, Sun E, Di Mascio M, Perelson A S, et al. A novel antiviral intervention results in more accurate assessment of human immunodeficiency virus type 1 replication dynamics and T-cell decay in vivo. J Virol. 2003 April; 77(8):5037-5038.
70. Vonesh E F, Chinchilli V M. Linear and nonlinear models for the analysis of repeated measurements. vol. 154 of Statistics: Textbooks and Monographs. New York: Marcel Dekker Inc.; 1997. With 1 IBM-PC floppy disk (3.5 inch; HD).
71. Davidian M, Giltinan D M. Nonlinear Models for Repeated Measurement Data (Chapman & Hall/CRC Monographs on Statistics & Applied Probability). 1st ed. New York: Chapman and Hall/CRC; 1995.
72. Wu H. Statistical methods for HIV dynamic studies in AIDS clinical trials. Statistical Methods in Medical Research. 2005; 14:171-192.
73. Bortz D. Model selection and mixed-effects modeling of HIV infection dynamics. Bulletin of Mathematical Biology. 2006; 68:2005-2025.
74. Wu L, Wu H. Missing Time-Dependent Covariates in Human Immunodeficiency Virus Dynamic Models. Journal of the Royal Statistical Society Series C (Applied Statistics). 2002 January; 51(3):297-318.
75. Huang Y, Wu H, Acosta E P. Hierarchical Bayesian inference for HIV dynamic differential equation models incorporating multiple treatment factors. Biom J. 2010 July; 52(4):470-486.
76. Samson A, Lavielle M. Extension of the SAEM algorithm to left-censored data in nonlinear mixed-effects model: Application to HIV dynamics model. Computational Statistics & Data Analysis. 2006 December; 51(3): 1562-1574.
77. Wu H, Zhao C, Liang H. Comparison of Linear, Nonlinear and Semiparametric Mixed-effects Models for Estimating HIV Dynamic Parameters. Biom J. 2004 April; 46(2):233-245.
78. Putter H, Heisterkamp S H, Lange J M A, de Wolf F. A Bayesian approach to parameter estimation in HIV dynamical models. Stat Med. 2002 August; 21(15):2199-2214.
79. Han C, Chaloner K, Perelson A. Bayesian analysis of a population HIV dynamic model. In: Gatsonis C, Kass R E, Carriquiry A, Gelman A, Higdon D, Pauler D K, et al., editors. Case Studies in Bayesian Statistics. New York: Springer; 2002. p. 223-237.
80. DiStefano J I, Cobelli C. On parameter and structural identifiability: Nonunique observability/reconstructibility for identifiable systems, other ambiguities, and new definitions. Automatic Control, IEEE Transactions on. 1980; 25(4):830-833.
81. Miao H, Dykes C, Demeter L, Wu H. Differential equation modeling of HIV viral fitness experiments: model identification, model selection, and multimodel inference. Biometrics. 2009; 65:292-300.
82. Wu H, Zhu H, Miao H, Perelson A S. Parameter identifiability and estimation of HIV/AIDS dynamic models. Bull Math Biol. 2008 April; 70(3):785-799.
83. Miao H, Xia X, Perelson A S, Wu H. On Identifiability Of Nonlinear ODE Models And Applications In Viral Dynamics. SIAM Rev Soc Ind Appl Math. 2011 January; 53(1):3-39.
84. Besson G J, McMahon D, Maldarelli F, Mellors J W. Short-Course Raltegravir Intensification Does Not Increase 2 Long Terminal Repeat Episomal HIV-1 DNA in Patients on Effective Antiretroviral Therapy. Clinical Infectious Diseases. 2012 January; 54(3):451-453.
85. Wong J K, Ignacio C C, Torriani F, Havlir D, Fitch N J, Richman D D. In vivo compartmentalization of human immunodeficiency virus: evidence from the examination of pol sequences from autopsy tissues. J Virol. 1997 March; 71(3):2059-2071.
86. Zhu T, Wang N, Carr A, Nam D S, Moor-Jankowski R, Cooper D A, et al. Genetic characterization of human immunodeficiency virus type 1 in blood and genital secretions: evidence for viral compartmentalization and selection during sexual transmission. J Virol. 1996 May; 70(5):3098-3107.
87. Yukl S A, Shergill A K, McQuaid K, Gianella S, Lampiris H, Hare C B, et al. Effect of raltegravir-containing intensification on HIV burden and T-cell activation in multiple gut sites of HIV-positive adults on suppressive antiretroviral therapy. AIDS. 2010 October; 24(16): 2451-2460.
88. Buzón M J, Codoñr F M, Frost S D W, Pou C, Puertas M C, Massanella M, et al. Deep Molecular Characterization of HIV-1 Dynamics under Suppressive HAART. PLoS Pathog. 2011 October; 7(10):e1002314.

TABLE 1

Parameter definitions and units, Equation 1

| Parameter | Definition | Units |
|---|---|---|
| y | Concentration of active infected cells in the site of 2-LTR formation. | $\frac{\text{Infected Cells}}{10^6 \text{ PBMC}}$ |
| c | Concentration of 2-LTR circle as measured in the blood. | $\frac{\text{2-LTR Circles}}{10^6 \text{ PBMC}}$ |
| R | Probability, at the pre-intensification equilibrium, of an actively infected cell successfully infecting a target cell in a single generation. | Unitless |
| a | Death rate of we infected cells. | $\frac{1}{\text{day}}$ |
| $y_e$ | Rate of production of actively infected cells by processes other than infection, including quiescent cell activation. | $\frac{\text{Infected Cells}}{10^6 \text{ PBMC} \times \text{day}}$ |
| $\eta_{II}$ | The ratio-reduction R following raltegravir intensification. Equivalent to the drug efficacy of raltegravir. | Unitless |
| $u_{II}$ | A binary variable which is 1 when raltegravir is applied and 0 when it is not applied. | Unitless |

TABLE 1-continued

Parameter definitions and units, Equation 1

| Parameter | Definition | Units |
|---|---|---|
| $\varphi$ | The ratio of the probabilay of 2-LTR Circle formation during an infection event when raltegravir is not present to the probability of 2-LTR. formation when raltegravir interrupts an infection event. | Unitless |
| $k_{II}$ | The probability of 2-LTR Circle formation when raltegravir interrupts an infection event. | $\dfrac{\text{2-LTR Circles}}{\text{Infected Cells}}$ |
| $\delta$ | Decay rate of 2-LTR Circles. | $\dfrac{1}{\text{day}}$ |

TABLE 2

Experimental 2-LTR quantification data for the 13 patients with units 2-LTR per $10^6$ PBMC, as reported in [36, 37], adjusted for theoretical censoring limits.

| | Week Post-Intensification | | | | | |
|---|---|---|---|---|---|---|
| Patient # | 0 | 2 | 4 | 12 | 24 | 48 |
| 001-23 | <1.20 | 23.69 | — | <1.20 | <1.20 | <1.20 |
| 001-33 | 2.99 | 1.98 | 3.03 | — | <1.20 | <1.20 |
| 001-35 | <1.20 | 21.47 | <1.20 | — | — | — |
| 001-43 | 1.76 | 48.16 | — | 10.38 | 2.73 | <1.20 |
| 001-44 | 38.62 | 72.77 | <1.20 | 7.38 | 2.20 | — |
| 006-69 | 35.30 | 30.55 | 9.07 | 1.26 | <1.20 | — |
| 023-25 | <1.20 | 5.84 | 5.37 | <1.20 | 1.88 | <1.20 |
| 023-68 | 9.98 | 12.98 | 13.42 | 1.61 | <1.20 | <1.20 |
| 001-13 | <1.20 | 3.05 | 3.19 | <1.20 | 1.29 | 7.04 |
| 001-42 | — | <1.20 | <1.20 | 9.55 | <1.20 | <1.20 |
| 006-48 | <1.20 | <1.20 | 2.68 | 39.64 | <1.20 | <1.20 |
| 006-52 | <1.20 | <1.20 | 24.75 | 30.11 | <1.20 | <1.20 |
| 023-47 | <1.20 | <1.20 | 21.07 | <1.20 | <1.20 | <1.20 |

TABLE 3

Fitted Parameter Values

| Patient # | Parameter | Units | Median | MLE | 95% Credible Interval |
|---|---|---|---|---|---|
| All | $\varphi$ | — | 0.0019 | 0.0018 | [0.0011, 0.0037] |
| | $\delta$ | day$^{-1}$ | 0.47 | 0.46 | [0.36, 0.83] |
| 001-23 | R | — | 0.9995 | 0.9999 | [0.9975, 1.0000] |
| | $\eta_{II}$ | — | 0.12 | 0.08 | [0.04, 0.26] |
| | $\kappa_{II}y_e$ | 2-LTR circles × $(10^6$ PBMC$)^{-1}$ × day$^{-1}$ | 0.15 | 0.21 | [0.01, 0.62] |
| 001-33 | R | — | 0.9985 | 0.9990 | [0.9895, 0.9996] |
| | $\eta_{II}$ | — | 0.78 | 0.01 | [0.002, 0.99] |
| | $\kappa_{II}y_e$ | 2-LTR circles × $(10^6$ PBMC$)^{-1}$ × day$^{-1}$ | 0.59 | 0.51 | [0.23, 2.24] |
| 001-35 | R | — | 0.9988 | 0.9994 | [0.9901, 0.9998] |
| | $\eta_{II}$ | — | 0.21 | 0.19 | [0.12, 0.37] |
| | $\kappa_{II}y_e$ | 2-LTR circles × $(10^6$ PBMC$)^{-1}$ × day$^{-1}$ | 0.37 | 0.39 | [0.06, 1.41] |
| 001-43 | R | — | 0.9994 | 0.9997 | [0.9970, 0.9999] |
| | $\eta_{II}$ | — | 0.02 | 0.02 | [0.01, 0.13] |
| | $\kappa_{II}y_e$ | 2-LTR circles × $(10^6$ PBMC$)^{-1}$ × day$^{-1}$ | 0.55 | 0.68 | [0.09, 1.68] |
| 001-44 | R | — | 0.9999 | 0.9999 | [0.9997, 1.0000] |
| | $\eta_{II}$ | — | 0.53 | 0.49 | [0.36, 0.92] |
| | $\kappa_{II}y_e$ | 2-LTR circles × $(10^6$ PBMC$)^{-1}$ × day$^{-1}$ | 1.10 | 1.27 | [0.53, 2.22] |
| 006-69 | R | — | 0.9999 | 0.9999 | [0.9997, 1.0000] |
| | $\eta_{II}$ | — | 0.74 | 0.77 | [0.43, 0.99] |
| | $\kappa_{II}y_e$ | 2-LTR circles × $(10^6$ PBMC$)^{-1}$ × day$^{-1}$ | 0.90 | 0.87 | [0.42, 1.84] |
| 023-25 | R | — | 0.7633 | 0.9940 | [0.0425, 0.9972] |
| | $\eta_{II}$ | — | 0.38 | 0.05 | [0.03, 0.97] |
| | $\kappa_{II}y_e$ | 2-LTR circles × $(10^6$ PBMC$)^{-1}$ × day$^{-1}$ | 1.58 | 1.08 | [0.36, 55.5] |
| 023-68 | R | — | 0.9994 | 0.9999 | [0.9976, 0.9999] |
| | $\eta_{II}$ | — | 0.04 | 0.03 | [0.02, 0.07] |
| | $\kappa_{II}y_e$ | 2-LTR circles × $(10^6$ PBMC$)^{-1}$ × day$^{-1}$ | 0.21 | 0.29 | [0.02, 0.84] |
| 001-13 | R | — | 0.4822 | 0.1748 | [0.0241, 0.9670] |
| | $\eta_{II}$ | — | 0.39 | 0.01 | [0.01, 0.97] |
| | $\kappa_{II}y_e$ | 2-LTR circles × $(10^6$ PBMC$)^{-1}$ × day$^{-1}$ | 5.11 | 2.14 | [0.96, 387.2] |
| 001-42 | R | — | 0.4923 | 0.6345 | [0.0234, 0.9588] |
| | $\eta_{II}$ | — | 0.53 | 0.79 | [0.06, 0.97] |
| | $\kappa_{II}y_e$ | 2-LTR circles × $(10^6$ PBMC$)^{-1}$ × day$^{-1}$ | 1.92 | 0.80 | [0.47, 83.6] |
| 006-48 | R | — | 0.4790 | 0.2843 | [0.0270, 0.9558] |
| | $\eta_{II}$ | — | 0.50 | 0.01 | [0.02, 0.98] |
| | $\kappa_{II}y_e$ | 2-LTR circles × $(10^6$ PBMC$)^{-1}$ × day$^{-1}$ | 3.11 | 1.73 | [0.70, 160.2] |
| 006-52 | R | — | 0.4893 | 0.9017 | [0.0260, 0.9543] |
| | $\eta_{II}$ | — | 0.55 | 0.81 | [0.04, 0.98] |
| | $\kappa_{II}y_e$ | 2-LTR circles × $(10^6$ PBMC$)^{-1}$ × day$^{-1}$ | 2.79 | 1.41 | [0.70, 106.4] |
| 023-47 | R | — | 0.4997 | 0.5138 | [0.0262, 0.9639] |
| | $\eta_{II}$ | — | 0.53 | 0.99 | [0.05, 0.98] |
| | $\kappa_{II}y_e$ | 2-LTR circles × $(10^6$ PBMC$)^{-1}$ × day$^{-1}$ | 2.00 | 1.14 | [0.50, 68.1] |

TABLE 4

Estimated pre-intensification infected cell turnover rates in units of cells × day$^{-1}$, assuming $\kappa_{II}$ = 1 and an efective patient volume of 30 L.

| Patient # | Median | MLE | 95% Credible Interval |
|---|---|---|---|
| 001-23 | 1.0 × 10$^7$ | 1.1 × 10$^7$ | [4.0 × 10$^6$, 2.6 × 10$^7$] |
| 001-33 | 1.3 × 10$^7$ | 1.3 × 10$^7$ | [3.1 × 10$^6$, 5.1 × 10$^7$] |
| 001-35 | 9.7 × 10$^6$ | 1.1 × 10$^7$ | [2.4 × 10$^6$, 2.8 × 10$^7$] |
| 001-43 | 3.0 × 10$^7$ | 3.3 × 10$^7$ | [1.2 × 10$^7$, 6.3 × 10$^7$] |
| 001-44 | 3.1 × 10$^8$ | 2.8 × 10$^8$ | [1.1 × 10$^8$, 8.3 × 10$^8$] |
| 006-69 | 2.5 × 10$^8$ | 2.9 × 10$^8$ | [8.2 × 10$^7$, 7.2 × 10$^8$] |
| 023-25 | 4.9 × 10$^5$ | 2.5 × 10$^5$ | [1.1 × 10$^5$, 7.1 × 10$^6$] |
| 023-68 | 1.2 × 10$^7$ | 1.1 × 10$^7$ | [6.8 × 10$^5$, 2.4 × 10$^7$] |
| 001-13 | 4.5 × 10$^5$ | 2.5 × 10$^5$ | [1.2 × 10$^5$, 1.6 × 10$^7$] |
| 001-42 | 1.8 × 10$^5$ | 1.0 × 10$^5$ | [6.1 × 10$^4$, 3.1 × 10$^6$] |
| 006-48 | 2.7 × 10$^5$ | 2.0 × 10$^5$ | [9.0 × 10$^4$, 6.6 × 10$^6$] |
| 006-52 | 2.4 × 10$^5$ | 1.7 × 10$^5$ | [8.7 × 10$^4$, 3.9 × 10$^6$] |
| 023-47 | 1.9 × 10$^5$ | 1.2 × 10$^5$ | [6.5 × 10$^4$, 2.6 × 10$^6$] |

TABLE 5

Parameters values for HIV Dynamics from [56]

| Parameters | Value | Units |
|---|---|---|
| $\log_{10}(\lambda)$ | (1.54, 2.88) | $\log_{10}\left(\dfrac{\text{cells}}{\mu L \times \text{day}}\right)$ |
| $\log_{10}(d)$ | (−1.35, −0.34) | $\log_{10}\left(\dfrac{1}{\text{day}}\right)$ |
| $\log_{10}(\beta)$ | (−5.78, −5.23) | $\log_{10}\left(\dfrac{mL}{\text{copies} \times \text{day}}\right)$ |
| $\log_{10}(\alpha)$ | (−0.76, 0.42) | $\log_{10}\left(\dfrac{1}{\text{day}}\right)$ |
| $\log_{10}(\gamma)$ | (3.39, 4.00) | $\log_{10}\left(\dfrac{\text{copies} \times \mu L}{\text{cells} \times mL \times \text{day}}\right)$ |
| $\log_{10}(\omega)$ | 18.8 | $\log_{10}\left(\dfrac{1}{\text{day}}\right)$ |
| $\log_{10}(\eta)$ | (0.60, 0.89) | — |

TABLE 6

Parameter values for 2-LTR formation from [55]

| Parameters | Value | Units |
|---|---|---|
| $k_{II}$ | (270, 910) | $\dfrac{\mu L}{10^6 \text{PBMC}}$ |
| $k_{INT}$ | (0.54, 1.82) | $\dfrac{\mu L}{10^6 \text{PBMC}}$ |
| $\delta$ | 0.46 | $\dfrac{1}{\text{day}}$ |

What is claimed:

1. A method for determining a pre-intensification HIV infection success ratio (R) in a patient, wherein the patient has received a suppressive antiviral therapy not containing an HIV integrase inhibitor, and wherein the patient has undetectable plasma viremia, comprising:
   (a) making a pre-intensification measurement of the concentration of an episomal artifact in a pre-intensification sample from the patient;
   (b) administering to the patient the HIV integrase inhibitor in an effective amount for intensifying the suppressive antiviral therapy;
   (c) making one or more post-intensification measurements of the concentration of the episomal artifact in one or more post-intensification samples from the patient; and
   (d) computing, on at least one processor, the pre-intensification HIV infection success ratio (R) based on the pre-intensification measurement and the one or more post-intensification measurements in accordance with Equations 1-3, 19 and 21:

$$\dot{y} = -(1 - (1 - \eta_{II} u_{II})R)ay + y_e \quad (1)$$
$$\dot{c} = \phi k_{II}(1 - \eta_{II} u_{II})Ray + k_{II} \eta_{II} u_{II} Ray - \delta c$$

$$c(t) = c(\infty) + (c(0) - c(\infty))e^{-\delta t} + \quad (2)$$
$$c(\infty)\frac{\delta \eta_{II} R}{(1-R)(a(1-(1-\eta_{II})R)-\delta)}(e^{-\delta t} - e^{-a(1-(1-\eta_{II})R)t})$$

$$c(0) = \frac{k_{II} y_e \phi R}{\delta(1-R)} \quad (3)$$

$$c(\infty) = \frac{k_{II} y_e R(\phi + \eta_{II} - \delta \eta_{II})}{\delta(1-(1-\eta_{II})R)}$$

$$\sigma(c) = 10^{-0.21 - 0.24 \log_{10}(42 \times c)} \quad (19)$$

$$m_i(t_{i,k}) = \max\{c(t_{i,k}, \phi, A_{,i}, \eta_{IIi}, R_i) + e_{i,k}, 1.2\} \quad (21)$$
$$e_{i,k} \sim \mathcal{LN}(0, \sigma^2(c)),$$

wherein y is the concentration of actively infected cells in the site of the episomal artifact, c is the concentration of the episomal artifact as measured in the blood, t is the measurement time, a is the death rate of actively infected cells, $y_e$ is the rate of production of actively infected cells by processes other than infection, $\eta_{II}$ is the ratio-reduction in R following the intensification, $u_{II}$ is a binary variable, which is 1 when the HIV integrase inhibitor is applied and 0 when it is not applied; $\varphi$ is the ratio of the probability of the episomal artifact formation during an infection event when the HIV integrase inhibitor is not present to the probability of the episomal artifact formation when the HIV integrase inhibitor interrupts an infection event, $k_{II}$ is the probability of the episomal artifact formation when the HIV integrase inhibitor interrupts an infection event, $\delta$ is the decay rate of the episomal artifact, $m_i(t_{i,k})$ is the i-th patient's episomal artifact measurement at time $t_{i, k}$, and $e_{i, k}$ is log-normally distributed zero-mean measurement variance.

2. The method of claim 1, wherein when the pre-intensification HIV infection success ratio (R) in the patient is in the range from 0.95 to 1, the method further comprises quantifying efficient cryptic HIV replication in the patient.

3. The method of claim 1, wherein the patient has received the suppressive antiviral therapy for at least 6 months prior to the administration of the HIV integrase inhibitor.

4. The method of claim 1, wherein the HIV integrase inhibitor is raltegravir.

5. The method of claim 1, wherein the episomal artifact is selected from the group consisting of linear unintegrated HIV DNA, HIV 1-LTR DNA, and HIV 2-LTR circular DNA.

6. The method of claim 1, wherein each of the pre-intensification sample and the one or more post-intensification samples is a whole blood sample.

7. The method of claim 1, wherein the intensification lasts for at least 4 weeks.

8. The method of claim 1, wherein the one or more post-intensification measurements are made weekly.

9. The method of claim 1, wherein the one or more post-intensification measurements are 2 post-intensification measurements.

* * * * *